US011473051B2

(12) United States Patent
Hasunuma et al.

(10) Patent No.: US 11,473,051 B2
(45) Date of Patent: Oct. 18, 2022

(54) METHOD OF CULTIVATING ALGAE AND PHOTOBIOREACTOR

(71) Applicant: NICHIA CORPORATION, Anan (JP)

(72) Inventors: Tomohisa Hasunuma, Kobe (JP); Yuichi Kato, Kobe (JP); Yasuo Fujikawa, Yokohama (JP); Tomohiro Tsurumoto, Yokohama (JP)

(73) Assignee: NICHIA CORPORATION, Anan (JP)

( * ) Notice: Subject to any disclaimer, the term of this patent is extended or adjusted under 35 U.S.C. 154(b) by 0 days.

(21) Appl. No.: 16/802,037

(22) Filed: Feb. 26, 2020

(65) Prior Publication Data
US 2020/0270566 A1 Aug. 27, 2020

(30) Foreign Application Priority Data

Feb. 27, 2019 (JP) .............................. JP2019-034308
Jan. 31, 2020 (JP) .............................. JP2020-015613

(51) Int. Cl.
*C12N 1/12* (2006.01)
*C12N 13/00* (2006.01)
*A01G 33/00* (2006.01)
*C12M 1/00* (2006.01)

(52) U.S. Cl.
CPC .............. *C12N 1/12* (2013.01); *C12M 21/02* (2013.01); *C12N 13/00* (2013.01); *A01G 33/00* (2013.01)

(58) Field of Classification Search
CPC ...... C12N 1/12; C12N 13/00; C12N 15/8247; C12N 9/16; C12N 15/09; C12N 15/52; C12N 15/62; C12N 1/125; C12M 21/02; C12M 31/10; C12M 21/12; C12M 31/02; C12M 31/08; C12M 31/00; C12M 41/00; C12M 41/10; C12P 7/6463; C12P 23/00; C12P 7/649; C12P 7/64; C12P 17/165; C12P 19/04; C12P 21/00; C12P 5/007; C12P 5/026; C12P 7/021; A01G 33/00; A01G 7/045; A01G 9/20; Y02E 50/10; Y02E 50/13; Y02T 50/678; C12Y 301/02014; Y02P 60/14; Y02P 20/133; Y02P 20/134; H01L 25/0753; H01L 33/504; H01L 2933/0041; H05B 42/50; H05B 45/37; Y02A 40/80; A01H 3/02; C12R 2001/89; A23K 10/12; A23K 10/16; A23K 20/179; A23K 40/10; A23K 50/80; A23L 17/60; A23V 2002/00; A61K 31/01; A61K 31/045; A61K 31/409; A61K 36/05; A61K 47/10; A61K 47/26; A61K 8/11; A61K 8/31; A61K 8/34; A61K 8/345; A61K 8/4913; A61K 8/73; A61K 8/9722; A61K 9/0014; A61K 9/06; A01Q 17/04; A01Q 19/00; A01Q 19/007; A01Q 19/08; Y02B 20/30
See application file for complete search history.

(56) References Cited

U.S. PATENT DOCUMENTS

| | | | | |
|---|---|---|---|---|
| 9,567,615 B2* | 2/2017 | Davis | ..................... | C12N 15/09 |
| 9,750,105 B2* | 8/2017 | Rantala | .................. | H05B 45/37 |
| 9,816,079 B2* | 11/2017 | Davis | ..................... | C12P 7/6463 |
| 9,932,554 B2* | 4/2018 | Im | .......................... | C12M 31/02 |
| 10,104,740 B2* | 10/2018 | Rantala | .................. | A01G 7/045 |
| 10,398,000 B2* | 8/2019 | Rantala | .................. | A01G 7/045 |
| 10,479,969 B2* | 11/2019 | Kim | ....................... | C12N 1/12 |
| 2012/0088278 A1* | 4/2012 | Kim | ....................... | C12M 31/10 |
| | | | | 435/101 |
| 2012/0171733 A1* | 7/2012 | Im | .......................... | C12M 21/12 |
| | | | | 435/101 |
| 2014/0170733 A1* | 6/2014 | Shigyo | ...................... | C12N 1/12 |
| | | | | 435/257.3 |
| 2014/0215654 A1* | 7/2014 | Davis | ....................... | C12P 7/64 |
| | | | | 800/281 |
| 2014/0215916 A1* | 8/2014 | Ara | ........................ | A01G 7/045 |
| | | | | 47/58.1 LS |
| 2014/0234920 A1* | 8/2014 | Davis | ....................... | C12N 9/16 |
| | | | | 435/134 |

(Continued)

FOREIGN PATENT DOCUMENTS

CN 105925471 A 9/2016
JP 2002-315569 A 10/2002

(Continued)

OTHER PUBLICATIONS

Baba, et al., "Wavelength Specificity of Growth, Photosynthesis, and Hydrocarbon Production in the Oil-producing Green Alga *Botryococcus braunii*", Bioresource Technology 109: 266-270 (2012).
Brandt, et al., "Effect of Adaptation to Light of Different Spectral Composition on Photosynthesis of Chlorella Cells", Biofizika, 25(6): 1056-1059 (1980) (in Russian).
Matsui & Ohgai, "Studies on the Development of Technologies for Effective Utilization of Deep Ocean Resources (Phase 1)", Outcome Reports: 147-158 (1990) (in Japanese).

(Continued)

*Primary Examiner* — Michelle F. Paguio Frising
(74) *Attorney, Agent, or Firm* — Foley & Lardner LLP

(57) ABSTRACT

A method of cultivating algal cells of an algae belonging to a class selected from Chlorophyceae, Euglenophyceae, Bacillariophyceae and Haptophyceae includes: irradiating the algal cells with an artificial light having a ratio of (i) photon flux density in a wavelength range of 520-630 nm to (ii) photosynthetic photon flux density, that is 65% or more; and measuring a condition of the algal cells and/or a condition of an algal cell culture provided by cultivating the algal cells. Irradiation and non-irradiation of the algal cells with the artificial light are switched, or the photon flux density in the wavelength range of 520-630 nm is changed, according to the measured condition of the algal cells and/or the measured condition of the algal cell culture.

15 Claims, 15 Drawing Sheets

(56) References Cited

U.S. PATENT DOCUMENTS

| | | | |
|---|---|---|---|
| 2015/0140642 A1 | 5/2015 | Ohtake et al. | |
| 2015/0166947 A1* | 6/2015 | Ohtake | C12N 13/00 |
| | | | 435/257.1 |
| 2017/0107554 A1* | 4/2017 | Izumida | C12N 1/12 |
| 2018/0142197 A1* | 5/2018 | Im | C12P 7/649 |
| 2018/0171312 A1* | 6/2018 | Davis | C12Y 301/02014 |
| 2018/0371395 A9* | 12/2018 | Im | C12M 21/02 |
| 2020/0270566 A1* | 8/2020 | Hasunuma | C12M 31/00 |

FOREIGN PATENT DOCUMENTS

| | | |
|---|---|---|
| JP | 2003-169566 A | 6/2003 |
| JP | 2011-030463 A | 2/2011 |
| JP | 2012-163538 A | 8/2012 |
| JP | 2014-168409 A | 9/2014 |
| JP | 2017-163878 A | 9/2017 |
| JP | 6575987 B2 | 9/2019 |
| KR | 10-2016-0015941 A | 2/2016 |
| WO | WO-2014/119794 A1 | 8/2014 |
| WO | WO-2014/136574 A1 | 9/2014 |

OTHER PUBLICATIONS

Murase, et al., "Growth and Maturation of Gametophyte in Undaria pinnatifida under Different Light Quality from Light Emitting Diodes (LEDs)", Journal of National Fisheries University 67(2): 91-97 (2018) (in Japanese).

Okada, et al., "Effect of Monochromatic Lights by LEDs on the Growth and Changes of Intercellular Pigments in Chlorella vulgaris", Proceedings of the Annual Meeting of Chemical Society of Japan 81st No. 2: 1422 (2002) (in Japanese).

Takada, et al., "Growth and Photosynthesis of Ulva prolifera under Different Light Quality from Light Emitting Diodes (LEDs)", Aquaculture Sci. 59(1): 101-107 (2011) (in Japanese).

Wu, "Effect of Different Light Qualities on Growth, Pigment Content, Chlorophyll Fluorescence, and Antioxidant Enzyme Activity in the Red Alga Pyropia haitanensis (Bangiales, Rhodophyta)", BioMed Research International (2016), Article ID 7383918.

* cited by examiner

METHOD OF CULTIVATING ALGAE AND PHOTOBIOREACTOR

CROSS-REFERENCE TO RELATED APPLICATIONS

This application claims priority under 35 USC § 119 to Japanese Patent Application No. 2019-034308, filed on Feb. 27, 2019, and Japanese Patent Application No. 2020-015613, filed on Jan. 31, 2020, the contents of which are incorporated herein by reference in their entirety.

TECHNICAL FIELD

The present disclosure relates to a method and a photobioreactor for cultivating algae.

BACKGROUND

Microalgae, such as Haematococcus, *chlorella* and *euglena* algae, can produce ingredients of health food products and/or supplements, or oils suitable for biofuels, and therefore are cultivated enthusiastically.

Microalgae are cultivated in a closed system using an artificial light source (in a closed type photobioreactor, for example) or an open system utilizing sunlight (in an open pond, for example).

Cultivation in an open system is suitable for a large-scale cultivation. However, if the algae are not present at a certain concentration or more in the open system at the start of cultivation, they often cannot grow healthily because the amount of light to be irradiated per cell is too high. Accordingly, it is necessary to previously prepare a dense culture of microalgae at a certain concentration or more. Such a dense culture is often prepared in a closed system.

Thus, there is a need for a method of efficiently cultivating algae in a closed system.

In order to cultivate a large amount of algae efficiently and inexpensively throughout the year all day and night without being influenced by the cultivation location, Japanese Patent Publication No. 2002-315569 discloses a method of cultivating algae, characterized in that an algal culture is irradiated with monochromatic light (red or blue light) from a light emitting diode having a wavelength at which the specific absorbance of chlorophyll a contained in the algae is 60 or more, to promote the growth of the algae and keep the growth rate constant. The document also discloses a method of promoting photosynthesis, characterized in that the culture is irradiated with monochromatic light of 500 to 630 nm (green light, yellow light and orange light), which light is absorbed by phycocyanin (a phycobilin pigment).

Japanese Patent Publication No. 2011-30463 discloses an underwater lighting device including a blue LED and a red LED, for promoting photosynthesis of algae having chlorophyll. The document also discloses an underwater lighting device including a green LED, for promoting photosynthesis of algae having phycobilin.

PCT Publication WO 2014/119794 discloses a method of promoting growth of Chlorophyceaev, in which the growth of Chlorophyceae that is in a state of being a green swarm cell is promoted by irradiating the Chlorophyceae with an artificial light, wherein the Chlorophyceae are grown in a liquid medium while maintaining a state in which the color of a culture solution of the Chlorophyceae is green or brown by intermittently radiating a red illumination light while continuously radiating a blue illumination light.

Even if a large reactor vessel is used in the methods in order to provide efficient algal cultivation, light only reaches to a certain depth, so that light intensity per unit of cultivation medium is reduced in deep regions of the vessel. Consequently, the cell density is reduced in the deep regions of the reactor vessel. On the other hand, irradiation of microalgae with intense light to provide a high amount of photoenergy induces in the microalgae photo-oxidative stress (generation of active oxygen species), which has an adverse effect on growth of the microalgae cells.

In the methods described in the above-mentioned documents, red light and blue light are used to promote the photosynthesis in algal cells having chlorophyll. There are few studies about the effects of light of other colors on the photosynthesis in algal cells having chlorophyll.

Thus, there is still a need for a technique for efficiently cultivating microalgal cells.

SUMMARY

The present inventors investigated the wavelengths contributing to efficient cultivation of microalgal cells. As a result, the inventors have found that light in a range of 520 nm to 630 nm is more effective in biomass production in cells of an algae belonging to a class selected from Chlorophyceae, Euglenophyceae, Bacillariophyceae and Haptophyceae than red light, which has been conventionally used, thereby forming the basis of the present disclosure.

According to one embodiment, a method of cultivating algal cells of an algae belonging to a class selected from Chlorophyceae, Euglenophyceae, Bacillariophyceae and Haptophyceae includes irradiating the algal cells with an artificial light having a ratio of (i) photon flux density in the wavelength range of 520-630 nm to (ii) photosynthetic photon flux density, that is 65% or more; and measuring a condition of the algal cells and/or a condition of the algal cell culture. The irradiation and non-irradiation of the algal cells with the artificial light are switched, or the photon flux density in the wavelength range of 520-630 nm is changed, according to the measured condition of the algal cells and/or the measured condition of the algal cell culture.

According to another embodiment, a method comprises providing an algal cell culture including cultivating algal cells of an algae belonging to a class selected from Chlorophyceae, Euglenophyceae, Bacillariophyceae and Haptophyceae by the above-mentioned method.

According to another embodiment, a photobioreactor for cultivating algal cells includes: a reactor vessel, a lighting device, and a sensor. The reactor vessel is configured to contain algal cells of an algae belonging to a class selected from Chlorophyceae, Euglenophyceae, Bacillariophyceae and Haptophyceae, and a culture medium for the algal cells. The lighting device is configured to irradiate the reactor vessel, wherein the lighting device is capable of emitting light having a ratio of (i) photon flux density in the wavelength range of 520-630 nm to (ii) photosynthetic photon flux density, that is 65% or more. The sensor is configured to measure a condition of the algal cells and/or a condition of the algal cell culture in the reactor vessel. The control unit controls the light source according to the output of the sensor.

DETAILED DESCRIPTION

Figure 1A:
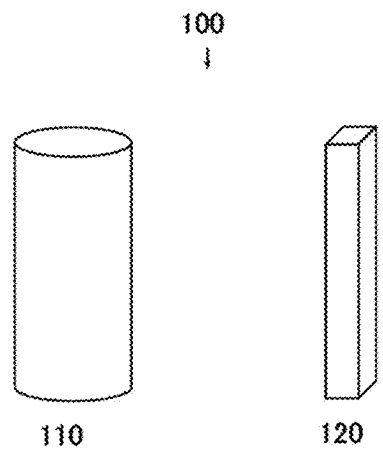
FIG. 1A illustrates a first embodiment of the photobioreactor according to the present invention.

Unless defined otherwise, all technical and scientific terms used herein have the same meaning as is commonly understood by one of ordinary skill in the art to which the present disclosure belongs. Although any apparatuses, devices, methods, and materials similar or equivalent to those described herein can be used in the practice or testing of the present disclosure, representative apparatuses, devices, methods, and materials are now described.

As used herein and the appended claims, the singular forms "a", "an" and "the" include plural referents unless the context clearly dictates otherwise. The terms "comprise", "comprising", "include," "including," "have," "has," "having," and the like are intended to be inclusive and mean that there may be additional elements other than the listed elements.

In the context of the present disclosure, the term "algae" is intended to mean algae belonging to a class selected from Chlorophyceae, Euglenophyceae, Bacillariophyceae and Haptophyceae.

As used herein, a numerical range "a to b" or "a-b" ("a" and "b" represent specific numerical values) means the range including both of the values "a" and "b", that is, the range "between a and b, both inclusive".

<Cultivation Method>

In one aspect, the present disclosure provides a method of cultivating algae belonging to a class selected from Chlorophyceae, Euglenophyceae, Bacillariophyceae and Haptophyceae.

A method of cultivating algal cells according to the disclosure (also referred herein to as "present cultivation method") includes irradiating the cells of an algae belong to a class selected from Chlorophyceae, Euglenophyceae, Bacillariophyceae and Haptophyceae with an artificial light having a ratio of (i) photon flux density in a wavelength range of 520 nm to 630 nm to (ii) photosynthetic photon flux density, that is 65% or more.

The disclosure is based on findings that irradiation of algal cells in culture with light in the wavelength range of 520 nm to 630 nm enables the algal cells to grow at an increased growth rate to a higher cell density, compared to when irradiated with red light, as shown in the Examples below. Thus, according to a method of the disclosure, the algal cells can be cultivated efficiently. Without wishing to be bound by any particular theory, the present inventors believe that the effect of the disclosure results partially from light in the specific wavelength range reaching deeper into the culture than red light.

As used herein, the term "artificial light" refers to light emitted by an artificial light source, and a light component of certain wavelengths extracted (by using an optical filter, for example) from natural light (mostly sunlight).

In the context of the artificial light, the term "ratio of photon flux density in the wavelength range of c-d to photosynthetic photon flux density" (wherein "c" and "d" indicate the lower and upper limit wavelengths (in nm), respectively, of a specific wavelength range) means a ratio value calculated from the following formula: [(photon flux density in the wavelength range of c–d)/(photosynthetic photon flux density)]×100(%). The "photosynthetic photon flux density" is the photon flux density of photosynthetically active components (in the wavelength range of 400 to 700 nm) of the artificial light.

In the context of present cultivation method, the "photon flux density" is a photon flux density measured at the light-receiving surface of the culture medium containing the algal cells to be irradiated. For example, the photon flux density at the light-receiving surface of the culture medium may be a photon flux density measured at an area on the outer surface of a photobioreactor vessel or container containing the culture medium.

The artificial light to be irradiated to the algal cells in the present invention has a ratio of (i) photon flux density in the wavelength range of 520-630 nm to (ii) photosynthetic photon flux density, that is 65% or more, more particularly 70% or more, more particularly 75% or more, more particularly 80% or more, more particularly 85% or more, more particularly 90% or more, and more particularly 95% or more.

In some embodiments, the artificial light has a ratio of (i) photon flux density in the wavelength range of 520-600 nm to (ii) photosynthetic photon flux density, that is 65% or more, more particularly 70% or more, more particularly 75% or more, more particularly 80% or more, more particularly 85% or more, more particularly 90% or more, and more particularly 95% or more. The embodiments can improve energy intensiveness, and cultivate the algal cells more efficiently.

Preferably, the artificial light has the maximum peak wavelength in the wavelength range of 520 to 630 nm, and more preferably in the wavelength range of 520 to 600 nm. Use of such an artificial light is preferable in that the algal cells can be efficiently irradiated with light in the wavelength range, which can grow the algal cells more efficiently than red light.

Accordingly, in some embodiments, the artificial light consists substantially of wavelengths from 520 to 630 nm, or from 520 to 600 nm. In some embodiments, the artificial light has a wavelength spectrum with a peak wavelength at 545±25 nm (and more preferably at 545±15 nm) and a half-width of 0.1 to 50 nm (and more preferably 0.1 to 20 nm).

The artificial light may be light emitted by a single light source, or a mixed or composite light emitted by two or more light sources. In the latter case, it is sufficient that the mixed or composite light, but not necessarily light emitted by each of the light sources (that is, each light to be mixed or made into composite), has a ratio of (i) photon flux density in the wavelength range of 520-630 nm (and more particularly 520-600 nm) to (ii) photosynthetic photon flux density, that is such a value as mentioned above (that is 65% or more, for example).

The artificial light may include light having a wavelength spectrum with a peak wavelength at 545±25 nm (and more preferably at 545±15 nm) and a half-width of 0.1 to 50 nm (and more preferably 0.1 to 20 nm). In other words, the artificial light may be such a mixed or composite light that is composed of light having a wavelength spectrum with a peak wavelength at 545±25 nm (and more preferably at 545±15 nm) and a half-width of 0.1 to 50 nm (and more preferably 0.1 to 20 nm), and light having a different wavelength spectrum.

Of the artificial light, light in the wavelength range of 520 to 630 nm (and more particularly 520 to 600 nm) may include, or consist of, light emitted by light-emitting diode (LED) or laser diode (LD). The use of LED light or LD light can suppress the radiation of red light and/or blue light that can have an adverse effect on the cells (such as cell damage by active oxygen species generated). Thus efficient irradiation with such light can allow the light to reach the algae in the inside of the culture (e.g., in the deeper parts of the culture when irradiated from the top, and in the central part and more distant parts of the culture when irradiated from the lateral direction). This can allow the light to be absorbed by chlorophylls, and thus, utilized for photosynthesis. In view of energy efficiency and economic efficiency, use of LED or LD is preferable due to the energy intensiveness, low heat generation, low power consumption, and long life. The use of LED or LD can also facilitate control and maintenance of photon flux density.

The value of photon flux density in the wavelength range of 520 to 630 nm (and more particularly 520 to 600 nm) is not particularly limited so long as it is effective in cultivating the algal cells. As used herein, the expression "effective in cultivating the algal cells" means that the culture does not intermittently decrease (preferably increases) in the number or density of algal cells therein. The value of photon flux density in the wavelength range of 520 to 630 nm (and more particularly 520 to 600 nm) may be, for example, 50-3000 $\mu mol/m^2/s$, more particularly 50-2000 $\mu mol/m^2/s$, more particularly 50-1000 $\mu mol/m^2/s$. Light at a photon flux density of less than 50 $\mu mol/m^2/s$ or more than 3000 $\mu mol/m^2/s$ may not efficiently cultivate the algal cells.

In some embodiments, the value of photon flux density in the wavelength range of 520 to 630 nm (and more particularly 520 to 600 nm) is 100 to 1000 $\mu mol/m^2/s$, more particularly 150 to 1000 $\mu mol/m^2/s$, more particularly 200 to 1000 $\mu mol/m^2/s$, more particularly 300 to 1000 $\mu mol/m^2/s$, and more particularly 300 to 900 $\mu mol/m^2/s$. In other embodiments, the value of photon flux density in the wavelength range of 520 to 630 nm (and more particularly 520 to 600 nm) is 50 to 500 $\mu mol/m^2/s$, more particularly 50 to 400 $\mu mol/m^2/s$, and more particularly 50-300 $\mu mol/m^2/s$.

An effective value of photon flux density in the wavelength range of 520 to 630 nm in cultivating algal cells can vary according to a condition(s) of the algal cells and/or the algal cell culture.

In one aspect, the present cultivation method is a method of cultivating algal cells of an algae belonging to a class selected from Chlorophyceae, Euglenophyceae, Bacillariophyceae and Haptophyceae, including:

irradiating the algal cells with an artificial light having a ratio of (i) photon flux density in the wavelength range of 520 to 630 nm to (ii) photosynthetic photon flux density, that is 65% or more; and measuring a condition of the algal cells and/or a condition of the algal cell culture, wherein the irradiation and non-irradiation of the algal cells with the artificial light are switched, or the photon flux density in the wavelength range of 520-630 nm is changed, according to the measured condition of the algal cells and/or the measured condition the algal cell culture.

In this aspect, the present cultivation method can provide the algal cells with light energy required for cell growth according to a condition(s) of the algal cells and/or a measured condition of the algal cell culture, and/or avoid excessive irradiation with light energy, resulting in inhibition of cell growth, thereby cultivating the algal cells more efficiently.

The condition of the algal cells and/or the condition of the algal cell culture can be, for example, at least one selected from the group consisting of cell density of the algal cell culture, singlet oxygen level of the algal cell culture, cell size of the algal cells and cell-cycle phase of the algal cells. In the present specification, the phrase "measuring a condition" can refer to the quantitative and semi-quantitative determination or estimation of, the detection of, or the monitoring of, one or more conditions of algal cells and/or algal cell culture.

For example, where the condition is the cell density of the algal cell culture, the effective photon flux density value in cultivating the algal cells at a cell density of a particular value or more can be greater than that at a cell density of less than the particular value. Irradiation of the algal cells at a low cell density with light in the wavelength range of 520 to 630 nm (and more particularly 520 to 600 nm) at a low photon flux density induces a high rate of cell growth without wasting energy. Meanwhile, irradiation of the algal cells at a high cell density with light in the wavelength range of 520 to 630 nm (and more particularly 520 to 600 nm) at a high photon flux density enables high density cultivation.

Thus, in some embodiments wherein the condition is the cell density of the algal cell culture, light of wavelengths from 520 to 630 nm (and more particularly 520 to 600 nm) is irradiated to the algal cells in culture at a photon flux density of 50 to 500 µmol m$^2$/s, more particularly 50 to 400 µmol/m$^2$/s, more particularly 50 to 300 µmol/m$^2$/s when the cell density of the culture is a predetermined value or less, and at a photon flux density of 300 to 3000 µmol/m$^2$/s, more particularly 300 to 2000 µmol/m$^2$/s, more particularly 300 to 1000 µmol/m$^2$/s, and more particularly 300 to 900 µmol/m$^2$/s when the cell density is the predetermined value or more.

In specific embodiments, light in the wavelength range of 520 to 630 nm (and more particularly from 520 to 600 nm) irradiates the algal cells at a first photon flux density value when the cell density is a predetermined value or less, and at a second photon flux density value, which is larger than the first photon flux density value, when the cell density is the predetermined value or more. The first photon flux density value may be, for example, 50 to 500 µmol/m$^2$/s, more particularly 50 to 400 µmol/m$^2$/s, and more particularly 50 to 300 µmol/m$^2$/s. The second photon flux density value may be, for example, 300 to 3000 µmol/m$^2$/s, more particularly 300 to 2000 µmol/m$^2$/s, more particularly 300 to 1000 µmol/m$^2$/s, and more particularly 300 to 900 µmol/m$^2$/s.

The "predetermined value" of cell density can be individually determined in preliminary cultivation of specific algal cells to be cultivated according to the present cultivation method. The predetermined value of cell density may, for example, be in the range of 0.5 to 5 g dry cell weight/L of culture medium, and more particularly 0.5, 0.8, 1, 1.2, 1.5, 1.8, 2, 2.2, 2.5, 2.8, 3, 3.2, 3.5, 3.8, 4, 4.2, 4.5, 4.8, or 5 g/L. Alternatively, the predetermined value of cell density may, for example, be in the range of $10^7$ to $10^8$ cells/mL of medium. The cell density of algal cells in culture can be determined by known methods, including cell counting based on electrical impedance measurement (Coulter principle), cell counting utilizing image recognition technique (such as TC20™ Automated Cell Counter, Bio-Rad), calculation from culture absorbance (measured at 750 nm or 560 nm, for example) or dry weight, which has been previously correlated with the foregoing cell counting.

In more specific embodiments, the present cultivation method is a method of cultivating algal cells of an algae belonging to a class selected from Chlorophyceae, Euglenophyceae, Bacillariophyceae and Haptophyceae, including: irradiating the algal cells with an artificial light having a ratio of (i) photon flux density in the wavelength range of 520 to 630 nm to (ii) photosynthetic photon flux density, that is 65% or more; and measuring a cell density of the algal cell culture, wherein the artificial light is irradiated so that the algal cells are irradiated with light n the wavelength range of 520 to 630 nm at a first photon flux density value when the measured cell density is a predetermined value or less, and at a second photon flux density value, which is larger than the first photon flux density value, when the measured cell density is above the predetermined value.

For example, where the condition is the singled oxygen level of the algal cell culture, the effective photon flux density value in cultivating the algal cells at a singlet oxygen level of more than a particular value can be smaller than the effective photon flux density value in cultivating the algal cells at a singlet oxygen level of less than the particular value.

Algal cells can produce singlet oxygen, which may induce cell damage, in photosynthesis (photosystem II), especially under strong light irradiation. Accordingly, the irradiation of the algal cell culture having a singlet oxygen level of less than a particular value with light in the wavelength range of 520 to 630 nm (and more particularly 520 to 600 nm) at a relatively high photon flux density value can induce a high rate of cell growth while reducing cell damage. Meanwhile, cell damage can be reduced by irradiating algal cell culture having a singlet oxygen level of more than the particular value with light in the wavelength range of 520 to 630 nm (and more particularly 520 to 600 nm) at a relatively low photon flux density value or by stopping the artificial light irradiation (preferably by placing the culture in dim light or darkness, and more preferably in darkness). In the present specification, the term "dim light" refers to such a level of photosynthetic photon flux density that does not cause a significant photooxidative stress in algal cells of interest, more specifically a photosynthetic photon flux density of <50 µmol/m$^2$/s, and more specifically a photosynthetic photon flux density of ≤10 µmol/m$^2$/s, and the term "darkness" or "dark" refers to such a level of photosynthetic photon flux density that does not cause photosynthesis in algal cells of interest, more specifically a photosynthetic photon flux density of ≤1 µmol/m$^2$/s.

During the irradiation at a relatively low photon flux density or stopping the artificial light irradiation, singlet oxygen, which has been generated by the irradiation at a relatively high photon flux density, diffuses and/or returns to the ground state and new generation of singlet oxygen is reduced or stopped, which results in reducing singlet oxygen level of the algal cell culture and therefore the risk of oxidative damage of the algal cells. According to this irradiation manner, cell damage can be reduced in the algal cell culture, thereby improving cultivation efficiency (in view of biomass productivity, for example).

Thus, in some embodiments wherein the condition is the singed oxygen level of the algal cell culture, the photon flux density in the wavelength range of 520-630 nm of the light irradiated to the algal cells is decreased or the irradiation of the algal cells with the artificial light is stopped when the singlet oxygen level is above a first predetermined value. Also, the photon flux density in the wavelength range of 520-630 nm is increased or the algal cells are irradiated with the artificial light when the singlet oxygen level is below a second predetermined value, which is smaller than the first predetermined value, or when a predetermined time period elapses after stopping the irradiation with the artificial light.

In some more specific embodiments, the present cultivation method is a method of cultivating algal cells of an algae belonging to a class selected from Chlorophyceae, Euglenophyceae, Bacillariophyceae and Haptophyceae, including:

irradiating the algal cells with an artificial light having a ratio of (i) photon flux density in the wavelength range of 520-630 nm to (ii) photosynthetic photon flux density, that is 65% or more; and measuring the singlet oxygen level of the algal cell culture, wherein the irradiation with the artificial light including:

a$_1$) irradiating with the light in the wavelength range of 520-630 nm at a first photon flux density value;

b$_1$) changing the photon flux density of light in the wavelength range of 520-630 nm from the first photon flux density value to a second photon flux density value, which is smaller than the first photon flux density value, once the measured singlet oxygen level is above a first predetermined value;

$c_1$) irradiating with the light in the wavelength range of 520-630 nm at the second photon flux density value;

$d_1$) changing the photon flux density of light in the wavelength range of 520-630 nm from the second photon flux density value to the first photon flux density value, once the measured singlet oxygen level is below a second predetermined value, which is smaller than the first predetermined value, or after the irradiation step $c_1$) is carried out for a predetermined time period; and $e_1$) irradiating with the light in the wavelength range of 520-630 nm at the first photon flux density value.

This method may further include a step $f_1$) of repeating the steps $b_1$) to $e_1$) one or more times after step $e_1$).

The first photon flux density value can be, for example, 300-3000 $\mu mol/m^2/s$, more particularly 300-2000 $\mu mol/m^2/s$, more particularly 300-1000 $\mu mol/m^2/s$, and more particularly 300-900 $\mu mol/m^2/s$. The second photon flux density value can be, for example, 50-500 $\mu mol/m^2/s$, more particularly, 50-400 $\mu mol/m^2/s$, and more particularly 50-300 $\mu mol/m^2/s$.

In other more specific embodiments, the present cultivation method is a method of cultivating algal cells of an algae belonging to a class selected from Chlorophyceae, Euglenophyceae, Bacillariophyceae and Haptophyceae, including:

irradiating the algal cells with an artificial light having a ratio of (i) photon flux density in the wavelength range of 520-630 nm to (ii) photosynthetic photon flux density, that is 65% or more; and measuring the singlet oxygen level of the algal cell culture, wherein the artificial light irradiation is stopped when the measured singlet oxygen level is above a first predetermined value, and recommenced when the measured singlet oxygen level is below a second predetermined value, which is smaller than the first predetermined value, or after the irradiation is stopped for a predetermined time period after stopping the artificial light irradiation.

In these specific embodiments, the value of photon flux density in the wavelength range of 520 to 630 nm can be, for example, 300-3000 $\mu mol/m^2/s$, more particularly 300-2000 $\mu mol/m^2/s$, more particularly 300-1000 $\mu mol/m^2/s$, and more particularly 300-900 $\mu mol/m^2/s$.

In more preferable embodiments, the algal cell culture is placed in dim light or darkness (preferably in darkness) during the artificial light irradiation is stopped.

In the present specification, the "predetermined value" in the context of singlet oxygen level of the culture can be determined in preliminary cultivation of specific algal cells to be cultivated according to the present cultivation method. The first predetermined value of singlet oxygen level can be in the range, for example, from 10 to 100 times, more specifically 10, 20, 30, 40, 50, 60, 70, 80, 90 or 100 times, of the singlet oxygen level of the algal cell culture cultivated in dim light or darkness (preferably in darkness). The second predetermined value of singlet oxygen level can be in the range, for example, from 1 to 5 times, more specifically 1, 2, 3, 4 or 5 times, of the singlet oxygen level of the algal cell culture cultivated in dim light or darkness (preferably in darkness). The singlet oxygen level of an algal cell culture can be determined by any known method, including spectrometric measurement (phosphorescence at 1270 nm) using a high-sensitivity near-infrared detection system (such as High Sensitivity NIR Quantum Efficiency Measurement System QE-5000, Otsuka Electronics Co., Ltd.) and fluorescence measurement using a singlet oxygen detection reagent, such as Singlet Oxygen Sensor Green (SOSG). The singlet oxygen level of the culture (or the culture medium) is preferably measured at the light-receiving surface of the culture medium containing the algal cells to be irradiated, where the artificial light can be irradiated at the highest photon flux density (and therefore the amount of singlet oxygen generated is considered to be highest).

In these embodiments, the "predetermined time period" is such a time period that is required for significantly reducing the singlet oxygen level of the culture, and can be determined in preliminary cultivation of specific algal cells to be cultivated according to the present cultivation method. The "predetermined time period" may be, for example, 1 minute to 12 hours, preferably 5 minutes to 10 hours, more preferably 10 minutes to 8 hours, more preferably 30 minutes to 6 hours, and more preferably 1 hour to 4 hours.

The singlet oxygen level can be reduced by feeding a singlet oxygen eliminator to the culture.

Thus, in some embodiments wherein the photon flux density of light in the wavelength range of 520-630 nm is changed according to condition(s) of the algal cells and/or the algal cell culture other than the singlet oxygen level of algal cell culture (for example, the cell density of the algal cell culture), the present cultivation method can further includes measuring the singlet oxygen level of the algal cell culture, wherein a singlet oxygen eliminator is fed to the algal cell culture when the measured singlet oxygen level is a predetermined value or more. The singlet oxygen eliminator includes, but not limited to, vitamin C and vitamin E. The amount of the singlet oxygen eliminator fed is not particularly limited so long as it can effectively reduce the single oxygen level of the culture.

For example, where the condition is the cell size of the algal cells, the effective photon flux density value in cultivating relatively large-sized algal cells can be smaller than that for relatively small-sized algal cells.

As can be seen from the data shown in the Examples below, cells with a high level of singlet oxygen generated tend to have an increased DNA content. Generally, cells with a increased DNA content trend to be large in size. Thus, it is reasonably expected that relatively small-sized cells, which contain a low level of singlet oxygen, can have the capacity of being irradiated with light in the wavelength range of 520 to 630 nm (and more particularly 520 to 600 nm) at a relatively high photon flux density. This means that irradiation at a relatively high photon flux density can induce a high rate of cell growth of relatively small-sized cells. Meanwhile, for relatively large-sized algal cells, which contain a high level of singlet oxygen, the risk of cell damage due to singlet oxygen that may be generated in the cells can be reduced by irradiating with light in the wavelength range of 520 to 630 nm (and more particularly 520 to 600 nm) at a relatively low photon flux density or by stopping the artificial light irradiation (preferably by placing the culture in dim light or darkness, and more preferably in darkness). According to this irradiation manner, cell damage can be reduced in algal cell culture, thereby improving cultivation efficiency.

Thus, in some embodiments wherein the condition is the cell size of the algal cells, the algal cells are classified on the basis of size, and the relatively small-sized algal cells (cells having a cell size of a predetermined value or less) are subjected to a step of irradiation with the light in the wavelength range of 520-630 nm at a relatively high photon flux density and the relatively large-sized algal cells (cells having a cell size of the predetermined value or more) are subjected to a step of irradiation with the light in the wavelength range of 520-630 nm at a relatively low photon flux density (which may be 0 μmol/m²/s; non-irradiation).

In the context of the cell size of algal cells, the "predetermined value" is a value capable of separating the cells with a high DNA content from the cells with a low DNA content. The predetermined value may be, for example, a value corresponding to two times of the cell volume when the algal cells are cultivated in dim light or darkness (preferably in darkness). The predetermined value can be determined in preliminary cultivation of specific algal cells to be cultivated according to the present cultivation method.

The size-classification of algal cells can be determined by any known method, including wet classification, dry classification, sieve size classification, and micro-channel classification. In the present disclosure, wet classification and sieve size classification are preferable. Wet classification can be carried out using a hydrocyclone (wet cyclone).

In some more specific embodiments, the present cultivation method is a method of cultivating algal cells of an algae belonging to a class selected from Chlorophyceae, Euglenophyceae, Bacillariophyceae and Haptophyceae, including:

irradiating the algal cells with an artificial light having a ratio of (i) photon flux density in the wavelength range of 520-630 nm to (ii) photosynthetic photon flux density, that is 65% or more;

size-classifying the algal cells between relatively small-sized algal cells and relatively large-sized algal cells; and subjecting the relatively small-sized algal cells to step $a_2$) as mentioned below and the relatively large-sized algal cells to step $b_2$) as mentioned below, wherein the irradiation with the artificial light includes:

the step $a_2$) of irradiating the relatively small-sized algal cells with the light in the wavelength range of 520-630 nm at a first photon flux density value; and the step $b_2$) of irradiating the relatively large-sized algal cells with the light in the wavelength range of 520-630 nm at a second photon flux density value, which is smaller than the first photon flux density value.

In further specific embodiments, this method can include a step of size-classifying the algal cells that have been subjected to the step $a_2$) or $b_2$), and again subjecting the classified cells to the step $a_2$) or $b_2$), which repetition step can be repeated two or more times.

The initial classification can be carried for classifying the algal cells that have been irradiated with the light in the wavelength range of 520-630 nm at a first photon flux density value.

In these specific embodiments, the first photon flux density value can be, for example, 300-3000 μmol/m²/s, more particularly 300-2000 μmol/m²/s, more particularly 300-1000 μmol/m²/s, and more particularly 300-900 μmol/m²/s. The second photon flux density value can be, for example, 50-500 μmol/m²/s, more particularly, 50-400 μmol/m²/s, and more particularly 50-300 μmol/m²/s.

The step $a_2$) is carried out for a first predetermined time period. The first predetermined time period is not particularly limited and can be, for example, 4-12 hours, more particularly 4-10 hours, more particularly 4-8 hours, more particularly 4-6 hours, and more particularly 4-5 hours.

The step $b_2$) is carried out for a second predetermined time period. The second predetermined time period can be a typical time period required for the cells with an increased DNA content to divide, and can be, for example, 4-12 hours, more particularly 4-10 hours, more particularly 4-8 hours, more particularly 4-6 hours, and more particularly 4-5 hours.

In other more specific embodiments, the present cultivation method is a method of cultivating algal cells of an algae belonging to a class selected from Chlorophyceae, Euglenophyceae, Bacillariophyceae and Haptophyceae, including:

irradiating the algal cells with an artificial light having a ratio of (i) photon flux density in the wavelength range of 520-630 nm to (ii) photosynthetic photon flux density, that is 65% or more; and size-classifying the algal cells between relatively small-sized algal cells and relatively large-sized algal cells, wherein the relatively small-sized algal cells are subjected to a step $a_2$) of irradiation with the artificial light and the relatively large-sized algal cells are subjected to a step $b_2$) of placement in dim light or darkness (preferably in darkness).

In further specific embodiments, this method can include a step of size-classifying the algal cells that have been placed in dim light or darkness, and again subjecting the classified cells to the step of irradiation with the artificial light or the step of placement in dim light or darkness. The steps can be repeated two or more times.

The initial classification can be carried for classifying the algal cells that have been irradiated with the artificial light.

In these embodiments, the photon flux density value of light in the wavelength range of 520 to 630 nm can be, for example, 300-3000 μmol/m²/s, more particularly 300-2000 μmol/m²/s, more particularly 300-1000 μmol/m²/s, and more particularly 300-900 μmol/m²/s.

The step of irradiation with the artificial light is carried out for a first predetermined time period as mentioned above. The step of placement in dim light or darkness is carried out for a second predetermined time period as mentioned above.

The steps $a_2$) and $b_2$) can be carried out in separate reactor vessels.

For example, where the condition is the cell-cycle phase of the algal cells, the effective photon flux density value in cultivating the algal cells in the S, G2 or M phase of cell-cycle can be smaller than that for the algal cells in the G1 phase.

As can be seen from the data shown in the Examples below, the cell-cycle progression of the cells with a high level of singlet oxygen generated are arrested at the S, G2 or M phase. Thus, irradiation of the culture containing a relatively large amount of the algal cells in the G1 phase (for example, the culture in which 50% or more of, more particularly 60% or more of, more particularly 70% or more of, more particularly 80% or more of, 90% or more of, the algal cells are in the G1 phase) with light in the wavelength range of 520 to 630 nm (and more particularly 520 to 600 nm) at a relatively high photon flux density value can induce a high rate of cell growth. Meanwhile, for the culture containing a relatively large amount of the algal cells in the S, G2 or M phase (for example, the culture in which 50% or more of, more particularly 60% or more of, more particularly 70% or more of, more particularly 80% or more of, 90% or more of, the algal cells are in the S, G2 or M phase), the risk of cell damage due to singlet oxygen that can be generated in the cells or the number of damaged cells can be reduced by irradiating with light in the wavelength range of 520 to 630 nm (and more particularly 520 to 600 nm) at a relatively low photon flux density value or by stopping the artificial light irradiation (preferably by placing the culture in dim light or darkness, and more preferably in darkness). By the irradiation at the relatively low photon flux density value or the non-irradiation (particularly by the placement in dim light or darkness), generation of the singlet oxygen in the cells can be also reduced to allow the cell-cycle to proceed again. According to this irradiation manner, cell damage can be decreased and/or the cell-cycle progression that has been arrested is restarted in the algal cell culture, thereby improving cultivation efficiency.

Thus, in some embodiments wherein the condition is the cell-cycle phase of the algal cells, the cells in the G1 phase are subjected to a step of irradiation with the light in the wavelength range of 520-630 nm at a relatively high photon flux density value and the cells in the S, G2 or M phase are subjected to a step of irradiation with the light in the wavelength range of 520-630 nm at a relatively low photon flux density value (which may be 0 $\mu mol/m^2/s$; non-irradiation) or a step of placement in dim light or darkness.

The cell-cycle phase can be determined by any known method, including, for example, cell sorting based on image recognition or chlorophyll fluorescence (see, for example, Japanese Patent KOKAI Publication No. 2012-163538 A).

In some embodiments wherein the condition is the cell-cycle phase of the algal cells, the present cultivation method can include synchronizing the cell-cycle phase of the algal cells prior to the irradiation with the artificial light.

By the synchronization of the cell-cycle phase of the algal cells before the irradiation with the artificial light, the timing of switching the irradiation and non-irradiation or changing the photon flux density value of light in the wavelength range of 520-630 nm can be determined without monitoring the cell-cycle phase.

In some more specific embodiments, the present cultivation method is a method of cultivating algal cells of an algae belonging to a class selected from Chlorophyceae, Euglenophyceae, Bacillariophyceae and Haptophyceae, including:

irradiating the algal cells with an artificial light having a ratio of (i) photon flux density in the wavelength range of 520-630 nm to (ii) photosynthetic photon flux density, that is 65% or more; and synchronizing the cell-cycle phase of the algal cells,
wherein the irradiation with the artificial light includes:
a step $a_3$) of irradiation with the light in the wavelength range of 520-630 nm at a first photon flux density value; and
a step $b_3$) of irradiation with the light in the wavelength range of 520-630 nm at a second photon flux density value, which is smaller than the first photon flux density value,
and wherein the synchronized algal cells are subjected to the step $a_3$) for a first predetermined time period and then to the step $b_3$) for a second predetermined time period, or are subjected to the step $b_3$) for the second predetermined time period and then to the step $a_3$) for the first predetermined time period.

In other more specific embodiments, the present cultivation method is a method of cultivating algal cells of an algae belonging to a class selected from Chlorophyceae, Euglenophyceae, Bacillariophyceae and Haptophyceae, including:

irradiating the algal cells with an artificial light having a ratio of (i) photon flux density in the wavelength range of 520-630 nm to (ii) photosynthetic photon flux density, that is 65% or more; and synchronizing the cell-cycle phase of the algal cells,
wherein the synchronized algal cells are subjected to a step $a_3$) of irradiation with the artificial light for a first predetermined time period and then to a step $b_3$) of placement in dim light or darkness for a second predetermined time period, or are subjected to the step $b_3$) for the second predetermined time period and then to the step $a_3$) for the first predetermined time period.

The step $a_3$) can be applied for a time period during which the synchronized algal cells are or are expected to be in the G1 phase and the step $b_3$) can be applied for a time period during which the synchronized algal cells are or are expected to be in the S to M phases.

In these embodiments, the first photon flux density value can be, for example, 300-3000 $\mu mol/m^2/s$, more particularly 300-2000 $\mu mol/m^2/s$, more particularly 300-1000 $\mu mol/m^2/s$, and more particularly 300-900 $\mu mol/m^2/s$. The second photon flux density value can be, for example, 50-500 $\mu mol/m^2/s$, more particularly, 50-400 $\mu mol/m^2/s$, and more particularly 50-300 $\mu mol/m^2/s$.

In the step $a_3$) of irradiation with the artificial light, the artificial light is irradiated so that light in the wavelength range of 520-630 nm is irradiated to the algal cells at a first photon flux density value as mentioned above.

The first predetermined time period can be a time period for which the algal cells may be in the G1 phase, and can be, for example, 16 to 20 hours, more particularly 18 to 20 hours, and more particularly 19 to 20 hours.

The second predetermined time period can be a time period for which the algal cells may be in the S to M phases, and can be, for example, 4 to 8 hours, more particularly 4 to 6 hours, and more particularly 4 to 5 hours.

The steps $a_3$) and $b_3$) can be repeated one or more times at, for example, a time cycle of the first time period/the second time period of 16/8 hours to 20/4 hours.

The synchronization of the cell-cycle phase can be carried out by arresting the cells at a certain phase of the cell-cycle and then synchronously restarting the cell-cycle, or by pre-cultivating the algal cells in a predetermined light/dark cycle.

Arresting the cell-cycle at a certain phase can be carried out by treating the cells with a cell-cycle synchronizing agent (also referred to as "cell-cycle arresting agent"). As the cell-cycle synchronizing agent, any cell-cycle synchronizing agents can be used, which are preferably agents capable of arresting the cells at the S phase or (more preferably) the M phase. Examples of cell-cycle synchronizing agent includes colchicine, demecolcine, colcemid, nocodazole, *vinca* alkaloids (including vinblastine and vincristine), rhizoxin and the like.

Pre-cultivation for synchronization of the cell-cycle phase can be carried out in a light/dark cycle of 20/4 hours to 18/6 hours, for example. In the context of the "light/dark cycle" for the pre-cultivation for synchronizing the cell-cycle phase, as used herein, the "light period" refers to a time period during which the algal cells are irradiated with light in the wavelength range of 520-630 nm (and more particularly 520 to 600 nm) at a first photon flux density value (for example, 300 $\mu mol/m^2/s$ or more) and the "dark period" refers to a time period during which the algal cells are irradiated with light in the wavelength range of 520-630 nm (and more particularly 520 to 600 nm) at a second photon flux density value (for example, less than 300 $\mu mol/m^2/s$), preferably are placed in dim light of dark and more preferably in dark. Preferably, the light/dark cycle is the same as the cycle of the first time period for the step $a_3$)/the second time period for the step $b_3$).

The time period of the artificial light irradiation of the algal cells is not particularly limited so long as it is effective in cultivating the algal cells. The time period of the artificial light irradiation may be, for example, from 4 to 400 hours, more particularly from 5 to 400 hours, more particularly from 6 to 300 hours, more particularly from 6 to 200 hours, more particularly from 6 to 150 hours, and more particularly from 6 to 100 hours.

The artificial light may be irradiated as continuous light or intermittent light (such as pulsed light; or continuous or pulsed light at a light:dark cycle of 4:20, 8:16, 12:12, 16:8 or 20:4 hours). The use of intermittent light can avoid or reduce a rise in temperature of the light source and/or the algal culture. The pulse width of the pulsed light may be, for example, 100 ms or less, more particularly 50 ms or less, more particularly 20 ms or less, more particularly 10 ms or less, and more particularly 5 ms or less. The duty ratio of the pulsed light may be, for example, 50% or less, more particularly 40% or less, more particularly 30% or less, more particularly 20% or less, more particularly 10% or less, and more particularly 5% or less.

The algal cells to be cultivated by the present cultivation method, which belong to a class selected from Chlorophyceae, Euglenophyceae, Bacillariophyceae and Haptophyceae, have a chlorophyll, but not a phycobilin, as a photosynthetic pigment.

Chlorophyceae algae are preferably unicellular. The Chlorophyceae algae that can be used in the present cultivation method are not particularly limited and include species of *Chlorella, Parachlorella, Pseudochlorella, Chlamydomonas, Heterochlamydomonas, Haematococcus, Dunaliella, Scenedesmus* or *Desmodesmus, Botryococcus, Monoraphidium, Chlorococcum, Chloromonas, Ankistrodesmus, Volvox*, for example.

The Euglenophyceae algae that can be used in the present cultivation method are not particularly limited and include species of *Euglena, Phacus, Trachelomonas*, for example.

Bacillariophyceae algae are preferably unicellular. The Bacillariophyceae algae that can be used in the present cultivation method are not particularly limited and include species of *Nitzschia, Phaeodactylum, Cylindrotheca, Chaetoceros, Thalassiosira, Cyclotella, Skeletonema, Odontella*, for example.

Haptophyceae algae are preferably unicellular. The Haptophyceae algae that can be used in the present cultivation method are not particularly limited and include species of *Isochrysis, Pleurochrysis, Pavlova, Emiliania, Phaeocystis, Prymnesium, Gephyrocapsa, Chrysochromulina*, for example.

The algae to be used are not only wild-type algae but also genetically-modified algae (such as those in which a particular gene has been deleted or introduced) so long as they have a chlorophyll, but not a phycobilin, as a photosynthetic pigment.

In some embodiments, the algae belong to a class of Chlorophyceae or Euglenophyceae.

In the present cultivation method, the algal cells are cultivated in a fluid culture medium. The cultivation may be carried out under natural light, or under a condition shielded from natural light.

The cultivation according to the present cultivation method may be carried out in an open system (e.g., an open-pond tank, raceway or a pond), or in a closed system (e.g., a photobioreactor such as a photobioreactor according to the disclosure as detailed below). The algal cells cultivated in a closed system according to the present cultivation method are transferred in an open system (e.g., an open-pond tank, raceway or a pond) and further cultivated therein. In this case, the cultivation in the open system may or may not be carried out according to the present cultivation method.

The (fluid) cultivation medium and cultivation conditions can be selected appropriately, from those for cultivating microalgal cells, according to the algal cells to be cultivated. Generally, the cultivation medium contains nitrogen and/or a nitrogen source, carbon and/or a carbon source (such as a carbonate, carbon dioxide or the like), trace metals (such as phosphor, potassium, calcium, magnesium, manganese, iron and the like), vitamins (such as thiamine, biotin, vitamin $B_{12}$ and the like) and others. Specific examples of cultivation medium include HSM medium, MBM medium, MCM medium, MDM medium, OHM medium, AF-6 medium, BG-11 medium, C medium, MC medium, VT medium, and modifications thereof. The cultivation temperature may be, for example, 15 to 35° C., more particularly 20 to 35° C., and more particularly 20 to 30° C. The pH may be, for example, 4-10, and more particularly 6-9. Preferably, the cultivation medium is aerated with carbon dioxide (at 1 to 10 v/v %). Microbubbled carbon dioxide may be fed into the cultivation medium.

In the present cultivation method, the algal cells can be cultivated at a cell density (concentration) of 0.01 to 10 g/L, for example. Where the cell density is, for example, 0.1-10 g/L, more particularly 0.2-10 g/L, more particularly 0.5-10 g/L, more particularly 0.8-10 g/L, and more particularly 1-10 g/L, the present cultivation method may cultivate the algal cells more efficiently (for example, at a higher growth rate and/or at a higher cell density) than otherwise.

The present cultivation method is preferably carried out by use of a photobioreactor according to the disclosure, which will be described below.

In another aspect, the present cultivation method is a method of cultivating algal cells of an algae belonging to a class selected from Chlorophyceae, Euglenophyceae, Bacillariophyceae and Haptophyceae, including:

irradiating the algal cells with an artificial light having a ratio of (i) photon flux density in the wavelength range of 520-630 nm to (ii) photosynthetic photon flux density, that is 65% or more; and measuring a singlet oxygen level of the algal cell culture, wherein a singlet oxygen eliminator is fed to the algal cell culture when the measured singlet oxygen level is a predetermined value or more.

As described above, algal cells may generate singlet oxygen, which may induce cell damage, in photosynthesis (photosystem II), especially under strong light irradiation. Accordingly, the feeding of a singlet oxygen eliminator to the algal cell culture having a singlet oxygen level of a particular value or more can reduce the singlet oxygen level in the culture, thereby lowering the risk of cell damage. Thus, the method can improve the efficiency of algal cell cultivation.

The artificial light and the photon flux density in the wavelength range of 520 to 630 nm (and more particularly 520 to 600 nm) of the artificial light are as described above.

The singlet oxygen level of an algal cell culture (or the culture medium) can be determined by any known method, including spectrometric measurement (phosphorescence at 1270 nm) using a high-sensitivity near-infrared detection system (such as High Sensitivity NIR Quantum Efficiency Measurement System QE-5000, Otsuka Electronics Co., Ltd.) and fluorescence measurement using a singlet oxygen detection reagent, such as Singlet Oxygen Sensor Green (SOSG). The singlet oxygen level of the culture (or the culture medium) is preferably measured at the light-receiving surface of the culture medium containing the algal cells to be irradiated, where the artificial light may be irradiated at the highest photon flux density (and therefore the amount of singlet oxygen generated is considered to be highest).

The "predetermined value" in the context of singlet oxygen level of the culture can be determined as described above.

The singlet oxygen eliminator includes, but not limited to, vitamin C and vitamin E. The amount of the singlet oxygen eliminator fed is not particularly limited so long as it can reduce significantly the single oxygen level of the culture.

In this method, the photon flux density value may be, for example, 300-3000 µmol/m²/s, more particularly 300-2000 µmol/m²/s, more particularly 300-1000 µmol/m²/s, and more particularly 300-900 µmol/m²/s.

<Culture Provision Method>

In another aspect, the present invention provides a method of providing a culture of cells of an algae belonging to a class selected from Chlorophyceae, Euglenophyceae, Bacillariophyceae and Haptophyceae.

The method of providing an algal cell culture according to the invention (also referred herein to as "present culture provision method") includes cultivating algal cells of an algae belonging to a class selected from Chlorophyceae, Euglenophyceae, Bacillariophyceae and Haptophyceae by the present cultivation method described in <Cultivation method> above.

The algal cells to be used in the present culture provision method belong to a class selected from Chlorophyceae, Euglenophyceae, Bacillariophyceae and Haptophyceae, as described in <Cultivation method> above.

The present culture provision method can provide an algal cell culture efficiently (in terms of time and/or cost, for example) and/or at a higher cell density (or with a high biomass productivity), and further lead to providing useful substances (such as astaxanthin, lutein and oils) contained in the algal cells at low cost.

The use of the algal cell culture provided by present culture provision method in a method of efficiently producing a useful material in algal cells by irradiation with red light and/or blue light may further improve the production efficiency. For example, the cell culture obtained by cultivating algal cells of a Chlorophyceae in the green stage according to the present cultivation method can be used in in the method described in the Japanese Patent No. 6575987. This may produce astaxanthin in the cells more efficiently.

<Photobioreactor>

In still another aspect, the present disclosure provides a photobioreactor for cultivating algal cells of an algae belonging to a class selected from Chlorophyceae, Euglenophyceae, Bacillariophyceae and Haptophyceae.

The algae photobioreactor according to the disclosure (also referred herein to as "present photobioreactor") includes:

a reactor vessel configured to contain cells of an algae belonging to a class selected from Chlorophyceae, Euglenophyceae, Bacillariophyceae and Haptophyceae, and a culture medium for the algal cells; and a lighting device configured to irradiate the reactor vessel with light and emit light having a ratio of (i) photon flux density in the wavelength range of 520-630 nm to (ii) photosynthetic photon flux density, that is 65% or more.

The present photobioreactor is suitable for carrying out the present cultivation method described above.

The algal cells suitable to be cultivated in the present photobioreactor belong to a class selected from Chlorophyceae, Euglenophyceae, Bacillariophyceae and Haptophyceae, as described in <Cultivation method> above.

The cultivation medium used in the present photobioreactor is as described in <Cultivation method> above.

The present photobioreactor will be now described with reference to FIGS. 1A to 1H.

The present photobioreactor (100, 200, 300, 400, 500, 600, 700, 800) includes at least one reactor vessel (110, 210, 310, 410, 510, 511, 610, 611, 710, 711, 810). The reactor vessel may be vessels that can be used as a photobioreactor for cultivating microalgal cells. The vessel has any appropriate shape, including for example, planer (such as flat panel), tubular (such as tube, hose or pipe), cylindrical (such as tank), bottle-shaped, dome-shaped, cuboid, polyhedron and others. The vessel may be a tubular vessel folded in a meandering shape. The vessel may be a plastic film tube. The reactor vessel may be formed using a glass or plastic with high visible light transmittance (such as acrylic resin, polyethylene, polypropylene, polycarbonate, polystyrene, polyvinyl chloride, nylon or the like). The vessel may have any appropriate size. An appropriate size can be determined according to the desired scale of the cultivation.

The reactor vessel has a first opening, through which the algal cells and the cultivation medium can be introduced in the vessel and the algal culture can be collected from the vessel. The first opening may be configured to be sealed after introducing the algal cells and the cultivation medium.

The reactor vessel may have a second opening to feed carbon dioxide into the inside thereof (preferably into the cultivation medium). The second opening may be configured to be connectable to a carbon dioxide-feeder (such as compressor or pump). The first opening may be used also for feeding carbon dioxide.

The reactor vessel may be provided with a stirrer capable of stirring the algal cells and the cultivation medium contained therein.

The present photobioreactor includes at least one lighting device (120, 220, 320, 420, 520, 521, 620, 720, 820). The present photobioreactor may include a single lighting device combined with one or more reactor vessels, or two or more lighting device combined with one or more reactor vessels.

The lighting device emits light (artificial light) having a ratio of (i) photon flux density in the wavelength range of 520-630 nm to (ii) photosynthetic photon flux density, that is 65% or more, more particularly 70% or more, more particularly 75% or more, more particularly 80% or more, more particularly 85% or more, more particularly 90% or more, and more particularly 95% or more. In the context of the present photobioreactor, the "photon flux density" is the one measured at the inner or outer surface (preferably, outer surface) of the reactor vessel to be irradiated with light from the lighting device (i.e., the artificial light).

In some embodiments, the lighting device emits light (artificial light) having a ratio of (i) photon flux density in the wavelength range of 520-600 nm to (ii) photosynthetic photon flux density, that is 65% or more, more particularly 70% or more, more particularly 75% or more, more particularly 80% or more, more particularly 85% or more, more particularly 90% or more, and more particularly 95% or more. The embodiments can improve energy intensiveness and cultivate the algae more efficiently.

Preferably, the lighting device emits light having the maximum peak wavelength in the wavelength range of 520 to 630 nm, and more preferably in the wavelength range of 520 to 600 nm. Use of such a lighting device is preferable in that the algal cells contained in the reactor vessel can be efficiently irradiated with light in the wavelength range, which can grow the algal cells more efficiently than red light.

Accordingly, in some embodiments, the lighting device emits light consisting of wavelengths from 520 to 630 nm or from 520 to 600 nm. In some embodiments, the lighting device emits only light having a wavelength spectrum with a peak wavelength at 545±25 nm (and more preferably at 545±15 nm) and a half-width of 0.1 to 50 nm (and more preferably 0.1 to 20 nm).

The lighting device may include a single light source, or two or more light sources (520, 521; FIG. 1E).

Where the lighting device has two or more light sources, it is sufficient that the mixed or composite light emitted from the lighting device to the reactor vessel (i.e., the mixed or composite light irradiated to the algal cells contained in the reactor vessel when used), but not necessarily light emitted by each of the light sources, has a ratio of (i) photon flux density in the wavelength range of 520-630 nm (and more particularly 520-600 nm) to (ii) photosynthetic photon flux density, that is such a value as mentioned above (that is 65% or more, for example). Examples of the light source include light-emitting devices (LEDs), laser diodes (LDs), sodium lamps (such as low-pressure Na lamps), xenon lamps, fluorescent lamps, incandescent lamps, white lamps, metal halide lamps, high-pressure mercury lamps, and the like.

The lighting device includes at least one light source that emits at least light (or light component) of wavelengths from 520 to 630 nm (and more particularly from 520 to 600 nm). The light source may be any light source as listed above. Where light emitted by the light source used has a ratio of (i) photon flux density in the wavelength range of 520-630 nm (and more particularly 520-600 nm) to (ii) photosynthetic photon flux density, that is less than 65%, a filter may be arranged in front of a light emission surface of the light source, which filter has a transmittance in the wavelength range of 520 to 630 nm (and more particularly 520 to 600 nm) higher than that in the ranges of less than 520 nm and more than 630 nm. In view of energy efficiency, the lighting device preferably has such a light source that has a wavelength spectrum having a peak wavelength at 545±25 nm (and preferably at 545±15 nm) with a half-width of 0.1 to 50 nm (and preferably 0.1 to 20 nm) and more preferably the light source has a single peak in the emission spectrum.

In some preferred embodiments, the lighting device has such a light-emitting device (LED) or laser diode (LD) that emits light whose wavelength spectrum has a peak wavelength at 545±25 nm (and preferably at 545±15 nm) with a half-width of 0.1 to 50 nm (and preferably 0.1 to 20 nm). In this case, the lighting device may be provided as a cluster or an array of LDs or LEDs. The embodiments enable to suppress the radiation of red light and/or blue light that can have an adverse effect on the cells (such as cell damage by active oxygen species generated) at too high intensity. The embodiments also allow efficient irradiation with such light capable of reaching the algal cells in the central part and more distant parts (along the irradiation axis) of the cultivation medium containing the algal cells, which are contained in the reactor vessel, and of being absorbed (and utilized for photosynthesis) by chlorophylls. In view of energy efficiency and economic efficiency, use of LED or LD is preferable due to the energy intensiveness, low heat generation, low power consumption and long life. In addition, the photon flux density can be easily controlled and maintained.

The light source of the lighting device is situated so that the emitted light can be irradiated to the inside of the reactor vessel (and therefore the algal cells contained therein when used). The light source may be placed outside the reactor vessel, or inside the vessel (or in the cultivation medium when used), or both outside and inside the vessel. Where the light source is placed outside the reactor vessel, it is situated so that the emitted light can irradiate the reactor vessel in at least one direction of a downward direction (from the right above the vessel, for example), an upward direction (from beneath the vessel, for example) and a lateral direction (from right beside the vessel, for example).

The light source may have any configuration and can be designed appropriately according to the shape of the reactor vessel, the arrangement of the light source and the reactor vessel, and/or others. Specific examples of the light source may include a line light source and a panel light source.

Figure 1B:
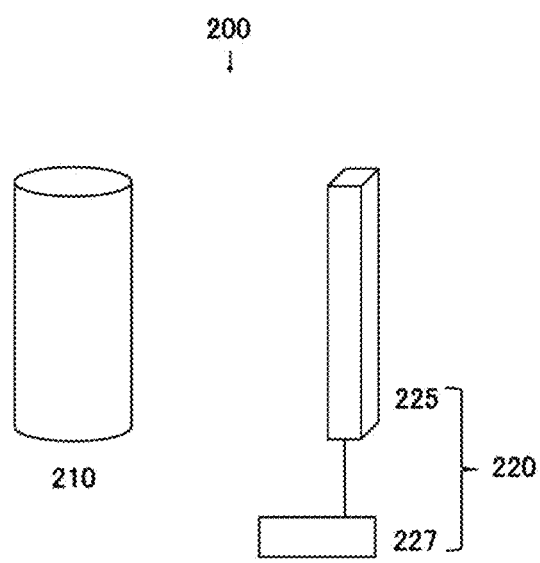
FIG. 1B illustrates a second embodiment of the photobioreactor according to the present invention.
Figure 1C:
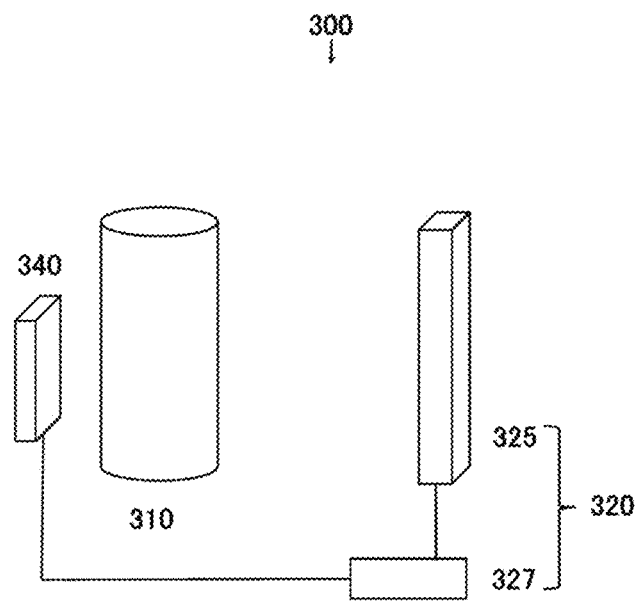
FIG. 1C illustrates a third embodiment of the photobioreactor according to the present invention.
Figure 1D:
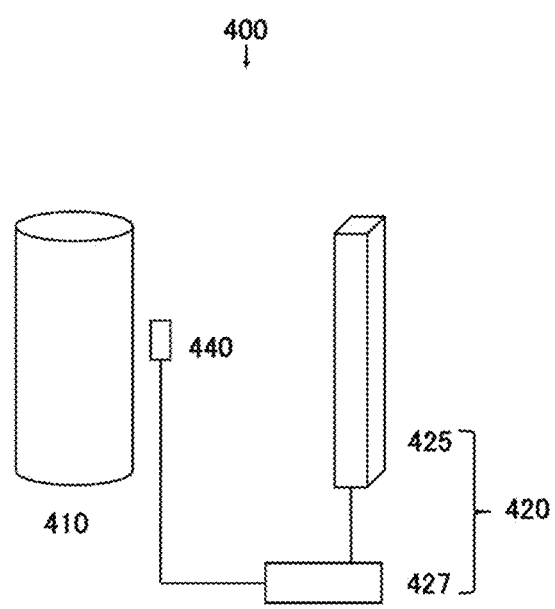
FIG. 1D illustrates a fourth embodiment of the photobioreactor according to the present invention.
Figure 1E:
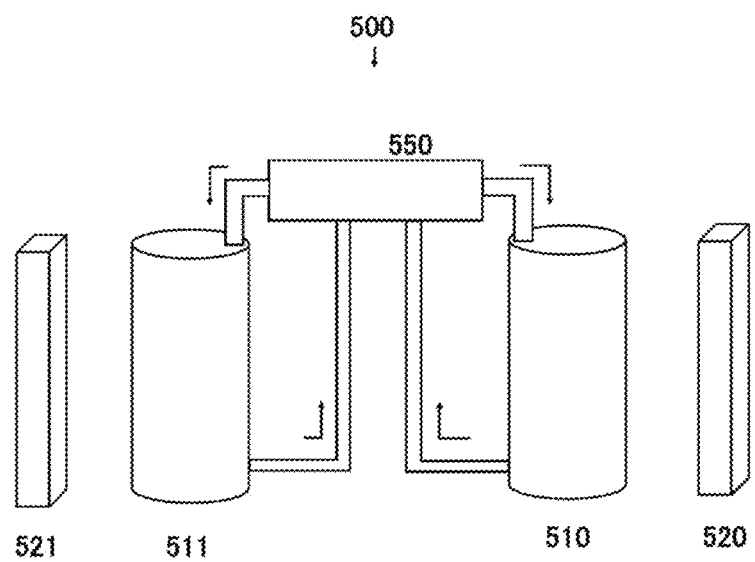
FIG. 1E illustrates a fifth embodiment of the photobioreactor according to the present invention.

The lighting device (220, 320, 420) may include a control unit (227, 327, 427) that controls the light source (225, 325, 425) (FIGS. 1B to 1D).

The control unit may control the light source of the lighting device so that light (which may be composite or mixed light) in the wavelength range of 520 to 630 nm (and more particularly 520 to 600 nm) emitted by the light source has a photon flux density value within a specified range.

Accordingly, in some embodiments, the lighting device includes: a light source capable of emitting light having a peak wavelength in the wavelength range of 520 to 630 nm (and more particularly 520 to 600 nm); and a control unit to control the light source to provide a photon flux density value within the specified range.

The control unit to control the dimming of the light source may be, for example, a pulse width modulation circuit.

The specified range is, for example, 50-3000 $\mu mol/m^2/s$, more particularly 50-2000 $\mu mol/m^2/s$, and more particularly 50-1000 $\mu mol/m^2/s$. Controlling the light source of the lighting device to provide a photon flux density value within the specified range enables the irradiation of the algal cells in the reactor vessel with light having a photon flux density value effective in cultivating the algal cells. A photobioreactor using light at a photon flux density of less than 50 $\mu mol/m^2/s$ or more than 3000 $\mu mol/m^2/s$ may not efficiently cultivate the algae.

In some certain embodiments, the control unit controls the light source to emit light having a photon flux density in the range of 520 to 630 nm (and more particularly from 520 to 600 nm) of 100-1000 $\mu mol/m^2/s$, more particularly 150-1000 $\mu mol/m^2/s$, more particularly 200-1000 $\mu mol/m^2/s$, more particularly 300-1000 $\mu mol/m^2/s$, and more particularly 300-900 $\mu mol/m^2/s$ or less. In other certain embodiments, the control unit controls the light source to emit light having a photon flux density in the range of 520 to 630 nm (and more particularly from 520 to 600 nm) of 50-500 $\mu mol/m^2/s$, more particularly 50-400 $\mu mol/m^2/s$ or less, and more particularly 50-300 $\mu mol/m^2/s$.

Additionally or alternatively, the control unit may control the irradiation time of the light source of the lighting device (particularly light source emitting light in the wavelength range of 520 to 630 nm, and more particularly 520 to 600 nm) within a specified range.

Accordingly, in some embodiments, the lighting device includes: a light source capable of emitting light having a peak wavelength in the wavelength range of 520 to 630 nm (and more particularly 520 to 600 nm); and a control unit to control the light source to emit light in the wavelength range of 520 to 630 nm (and more particularly 520 to 600 nm) for a predetermined period of time.

The control unit to control the irradiation time of the light source may be, for example, a timer.

The predetermined time period may be, for example, from 4 to 400 hours, more particularly from 5 to 400 hours, more particularly from 6 to 300 hours, more particularly from 6 to 200 hours, more particularly from 6 to 150 hours, and more particularly from 6 to 100 hours.

In some certain embodiments, the control unit controls the light source of the lighting device to emit light having a photon flux density in the range of 520 to 630 nm (and more particularly from 520 to 600 nm) of within the specified range, for the specified time period time, as described above. Such a control unit may include, for example, a timer and a pulse width modulation circuit.

The lighting device may emit light from the light source as continuous light or intermittent light (such as pulsed light; or continuous or pulsed light at a light:dark cycle of 4:20, 8:16, 12:12, 16:8 or 20:4 hours). The use of intermittent light can avoid or reduce a rise in temperature of the light source and/or the algal culture.

Where light emitted from the lighting device is a mixture of continuous and intermittent light components, it is preferable that light in the wavelength range of 520 to 630 nm (and more particularly 520 to 600 nm) is emitted intermittently.

The pulsed light may have a pulse width of, for example, 100 ms or less, more particularly 50 ms or less, more particularly 20 ms or less, more particularly 10 ms or less, and more particularly 5 ms or less. The pulsed light may have a duty ratio of, for example, 50% or less, more particularly 40% or less, more particularly 30% or less, more particularly 20% or less, more particularly 10% or less, and more particularly 5% or less.

As described above, an effective value of photon flux density in the wavelength range of 520 to 630 nm in cultivating algal cells can vary according to a condition(s) of the algal cells and/or the algal cell culture. The condition is at least one selected from the group consisting of cell density (concentration) of the algal cell culture, singlet oxygen level of the algal cell culture, cell size of the algal cells and cell-cycle phase of the algal cells, contained in the reactor vessel.

Accordingly, the present photobioreactor (300, 400) can be provided with a sensor (340, 440) configured to measure or sense a condition of the algal cells and/or a condition of the algal cell culture contained in the reactor vessel, and the light source (325, 425) of the lighting device (320, 420) can be controlled according to the output of the sensor (340, 440)(FIGS. 1C, 1D).

Thus, in some specific embodiments, the present photobioreactor (300, 400) includes:

a reactor vessel (310, 410) configured to contain cells of an algae belonging to a class selected from Chlorophyceae, Euglenophyceae, Bacillariophyceae and Haptophyceae, and a culture medium for the algal cells;

a lighting device (320, 420) configured to irradiate the reactor vessel with light having a ratio of (i) photon flux density in the wavelength range of 520-630 nm to (ii) photosynthetic photon flux density, that is 65% or more, which lighting device includes a light source (325, 425) capable of emitting light with a peak wavelength in the wavelength range of 520-630 nm and a control unit (327, 427) to control the light source; and a sensor (340, 440) configured to measure a condition(s) of the algal cells and/or the algal cell culture in the reactor vessel, wherein the control unit (327, 427) controls the light source (325, 425) according to the output of the sensor (340, 440)(FIGS. 1C, 1D).

The control unit can control the light source to change the photon flux density of light (particularly in the wavelength range of 520 to 630 nm, and more particularly 520 to 600 nm) emitted by the light source, according to the output of the sensor.

The sensor can be a photosensor, for example. The photosensor can be a photosensor configured to detect light from the inside of the reactor vessel.

The photosensor senses or measures the amount of light associated with the condition(s) of the algal cells and/or the algal cell culture in the reactor vessel. For example, the photosensor detects light from the inside of the reactor vessel, such as light passing through the inside of the vessel (and therefore transmitted through at least a portion of the cultivation medium contained in the vessel), or fluorescence or phosphorescence excited in the reaction vessel (i.e., in the culture medium) by excitation light. The photosensor (or light-receiving element) can be, for example, a photodiode, a photomultiplier, a spectrophotometer, a fluorometer, CCD, CMOS, a photoresistor or the like.

Transmitted, reflected, scattered or excitation light can originate from light irradiated to the reactor vessel for cultivating the algal cells therein (i.e., for photosynthesis in the algal cells), or from light irradiated only for measuring the condition of the algal cells and/or the condition of the algal cell culture.

For example, in embodiments wherein the photon flux density (particularly in the wavelength range of 520 to 630 nm, and more particularly 520 to 600 nm) of light emitted by the light source of the lighting device is changed according to the cell density (concentration) of the algal cell culture in the reactor vessel, the photosensor (340) is used to measure the absorbance (at 750 nm, in particular) of the algal cell culture in the reactor vessel (FIG. 1C).

For example, in embodiments wherein the photon flux density is changed according to the singlet oxygen level of the algal cell culture in the reactor vessel, the photosensor (440) is used to measure the phosphorescence (at 1270 nm, in particular) from the culture medium (at the light-receiving surface) in the reactor vessel (FIG. 1D).

When receiving light, the photosensor transmits the output according to the light intensity to the control unit of the lighting device, and the control unit controls the light source according to the output. For example, the control unit compares the output from the photosensor with a predetermined threshold value. When the output from the photosensor is above or below the threshold value, the control unit controls the light source to provide a photon flux density value with the predetermined ranges, or to switch the light source on and off.

For example, in embodiments wherein the photon flux density is changed according to the cell density (concentration) of the algal cell culture in the reactor vessel, the predetermined threshold value may be, for example, a value corresponding to 0.5 to 5 g dry weight/L of medium, more specifically 0.5, 0.8, 1, 1.2, 1.5, 1.8, 2, 2.2, 2.5, 2.8, 3, 3.2, 3.5, 3.8, 4, 4.2, 4.5, 4.8, or 5 g/L. Alternatively, the predetermined threshold value can be, for example, a value corresponding to $10^7$ to $10^8$ cells/mL of medium.

For example, when the output from the photosensor is above or below the threshold value (or when the output indicates that the cell density is the predetermined value or less), the control unit of the lighting device controls the light source to emit light (particularly in the range of 520 to 630 nm and more particularly from 520 to 600 nm) to the reactor vessel at a first photon flux density value of 300-3000 µmol/m$^2$/s. More particularly, the first photon flux density can be 300-2000 µmol/m$^2$/s, more particularly 300-1000 µmol/m$^2$/s, and more particularly 300-900 µmol/m$^2$/s.

Meanwhile, when the output from the photosensor is below or above the threshold value (or when the output indicates that the cell density is the predetermined value or more), the control unit controls the light source to emit light to the reactor vessel at a second photon flux density value of 50-500 μmol/m$^2$/s, or to switch the light source off. The second photon flux density value is less than the first photon flux density value. More particularly, the second photon flux density can be 50-400 μmol/m$^2$/s, and more particularly 50-300 μmol/m$^2$/s.

Figure 1F:
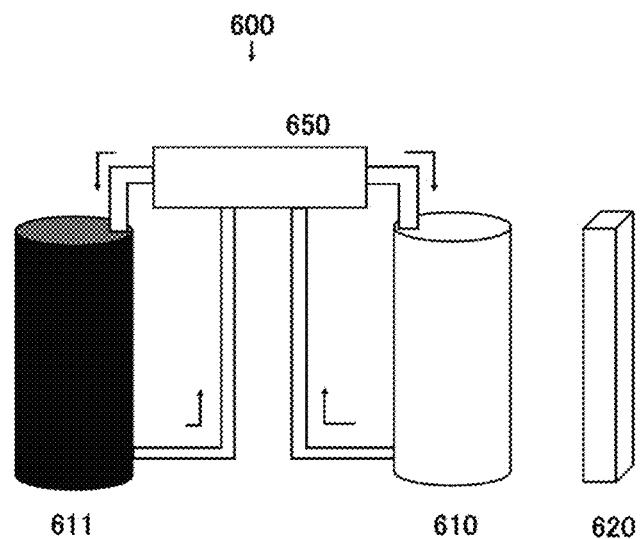
FIG. 1F illustrates a sixth embodiment of the photobioreactor according to the present invention.
Figure 1G:
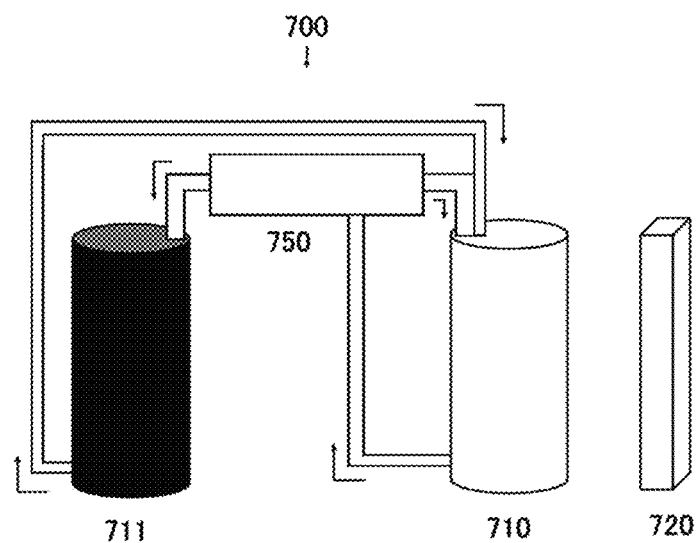
FIG. 1G illustrates a seventh embodiment of the photobioreactor according to the present disclosure.

The present photobioreactor (500, 600, 700) can include a size classifier (550, 650, 750) configured to classify the algal cells by size, the classified algal cells are irradiated with light (particular in the range of 520 to 630 nm and more particularly from 520 to 600 nm) emitted by the light source at respective photon flux density values effective in cultivating the classified algal cells (FIGS. 1E to 1G).

Thus, in some specific embodiments, the present photobioreactor (500, 600, 700) includes:
a (first) reactor vessel (510, 610, 710) configured to contain cells of an algae belonging to a class selected from Chlorophyceae, Euglenophyceae, Bacillariophyceae and Haptophyceae, and a culture medium for the algal cells;
a (first) lighting device (520, 620, 720) configured to irradiate the reactor vessel with light having a ratio of (i) photon flux density in the wavelength range of 520-630 nm to (ii) photosynthetic photon flux density, that is 65% or more; and
a size classifier (550, 650, 750) configured to classify the algal cells by size,
wherein the size classifier is interconnected to the reactor vessel and the relatively small-sized algal cells classified by the size classifier are fed to the reactor vessel (510, 610, 710)(FIGS. 1E to 1G).

To the size classifier, the algal cells to be initially fed to the reactor vessel(s) can be fed.

The size classifier classifies the algal cells fed thereto between relatively large-sized cells and relatively small-sized cells.

In the context of the size classifier, the "predetermined value" can be a value capable of separating the cells with a high DNA content from the cells with a low DNA content. The size classifier can be any known size classifier, including wet classifiers, dry classifiers, sieve classifiers, and classifiers using micro-channels. In the context of the present disclosure, wet classifiers and sieve classifiers are preferable. Wet classifiers can be hydrocyclone (wet cyclone) classifiers.

The relatively small-sized algal cells (having a cell size of a predetermined value or less), which are classified by the size classifier, are fed through a first cell-feeding path to the (first) reactor vessel. The algal cells cultivated in the (first) reactor vessel can be fed into the size classifier through a first cell-withdrawing path by, for example, a pumping system. In this case, the pumping system can be controlled to feed the algal cells from the reactor vessel to the size classifier regularly, for example, every 4-6 hours, more particularly every 4-5 hours.

The (first) lighting device irradiates the (first) reactor vessel with light in the wavelength range of 520-630 nm at a (first) photon flux density value, which can be, for example, 300-3000 μmol/m$^2$/s, more particularly 300-2000 μmol m$^2$/s, more particularly 300-1000 μmol/m$^2$/s, and more particularly 300-900 μmol/m$^2$/s.

In these embodiments, the present photobioreactor (500, 600, 700) can include a second reactor vessel (511, 611, 711) configured to contain the algal cells and a/the culture medium for the algal cells (FIGS. 1E to 1G). The first reactor vessel (510, 610, 710) can be connected to the second reactor vessel (711) via the size classifier (750) (unidirectionally) or can be interconnected to the second reactor vessel (511, 611) via the size classifier (550, 650). The relatively small-sized algal cells classified by the size classifier are fed to the first reactor vessel and the relatively large-sized algal cells (having a cell size of a predetermined value or more) are fed to the second reactor vessel.

In some more specific embodiments, the present photobioreactor (500) can further include a second lighting device (521) configured to irradiate the second reactor vessel (511) with light (particularly in the wavelength range of 520-630 nm, and more particularly from 520 to 600 nm) (FIG. 1E). The second lighting device irradiates the second reactor vessel with light in the wavelength range of 520-630 nm at a second photon flux density value, which is smaller than the first photon flux density value. The second photon flux density can be, for example, 50-500 μmol/m$^2$/s, more particularly 50-400 μmol/m$^2$/s, and more particularly 50-300 μmol/m$^2$/s.

In other more specific embodiments, the second reactor vessel (611, 711) is placed in dim light or darkness, or alternatively is configured to prevent light from irradiating the inside of the second reactor vessel at a photosynthetic photon flux density of 50 μmol/m$^2$/s or more, particularly above 10 μmol/m$^2$/s, and more particularly 1 μmol/m$^2$/s or more (FIGS. 1F, 1G). For example, the second reactor vessel (611, 711) can be formed of, or covered or surrounded with, a material having a low visible light transmittance to make the inside of the second reactor vessel dim or dark (FIGS. 1F, 1G).

The second reactor vessel can be connected to the size classifier through a (second) cell-withdrawing path. The relatively small-sized algal cells classified by the size classifier are fed into the first reactor vessel through a third cell-feeding path and the relatively large-sized algal cells are fed into the second reactor vessel through a fourth cell-feeding path by, for example, a pumping system.

Alternatively, the second reactor vessel (711) can be connected through a cell-feeding path to the second reactor vessel (710) through or without being through the size classifier (FIG. 1G).

Figure 1H:
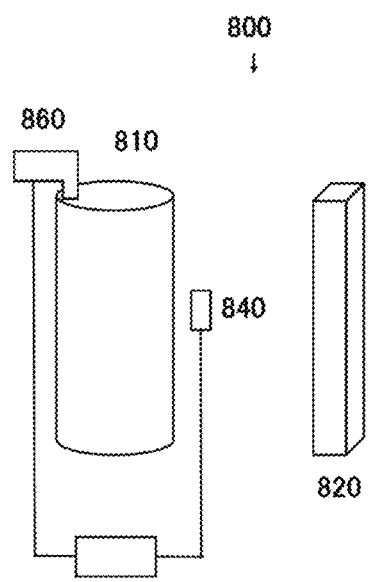
FIG. 1H illustrates an eighth embodiment of the photobioreactor according to the present disclosure.

The present photobioreactor (800) further include a sensor (840) configured to measure a singlet oxygen level in the reactor vessel and a singlet oxygen eliminator-feeder (860) configured to feed a singlet oxygen eliminator to the reactor vessel, wherein the singlet oxygen eliminator-feeder feeds the singlet oxygen eliminator to the reactor vessel according to measured singlet oxygen level in the reactor vessel (FIG. 1H).

Thus, in some specific embodiments, the present photobioreactor includes:
a reactor vessel configured to contain cells of an algae belonging to a class selected from Chlorophyceae, Euglenophyceae, Bacillariophyceae and Haptophyceae, and a culture medium for the algal cells;
a lighting device configured to irradiate the reactor vessel with light having a ratio of (i) photon flux density in the wavelength range of 520-630 nm to (ii) photosynthetic photon flux density, that is 65% or more;
a sensor configured to measure a singlet oxygen level in the reactor vessel; and
a singlet oxygen eliminator-feeder configured to feed a singlet oxygen eliminator to the reactor vessel, wherein the feeding of the singlet oxygen eliminator from the singlet oxygen eliminator-feeder to the reactor vessel is controlled according to the output of the sensor.

The sensor configured to measure the singlet oxygen level can be any known sensor that is capable of measuring the singlet oxygen level, preferably is a photosensor, which is as described above. The sensor is preferably provided to receive light from the artificial light-receiving surface of the culture liquid containing the algal cells to be irradiated. For example, it is situated facing the artificial light-receiving surface of the reactor vessel.

The singlet oxygen eliminator-feeder is not particular limited so long as it is configured to be capable of feeding a singlet oxygen eliminator to the reactor vessel. For example, the singlet oxygen eliminator-feeder includes a singlet oxygen eliminator-storage configured to store the singlet oxygen eliminator, and a singlet oxygen eliminator-feeding tube, one end of which is connected to the singlet oxygen eliminator-storage and the other end of which is connected to a discharge port configured to discharge the singlet oxygen eliminator to the reactor vessel. The feeding of the singlet oxygen eliminator from the singlet oxygen eliminator-storage to the discharge port can be conducted by, for example, a fluid transportation means, such as a pump, or an opening/closing system, such as a valve or a shutter, that is provided in the middle of the singlet oxygen eliminator-feeding tube. The timing and duration of pumping, or valve or shutter opening can be controlled according to the signal from the sensor.

The singlet oxygen eliminator includes, but not limited to, vitamin C and vitamin E. The amount of the singlet oxygen eliminator fed is not particularly limited so long as it can reduce efficiently the single oxygen level of the culture.

Non-limiting specific embodiments are described below:

Item 1:
A method of cultivating algal cells of an algae belonging to a class selected from Chlorophyceae, Euglenophyceae, Bacillariophyceae and Haptophyceae, comprising irradiating the algal cells with an artificial light having a ratio of (i) photon flux density in the wavelength range of 520-630 nm to (ii) photosynthetic photon flux density, that is 65% or more.

Item 2:
The method according to item 1, wherein the algae belong to Chlorophyceae or Euglenophyceae.

Item 3:
The method according to item 1 or 2, wherein the artificial light has a ratio of (i) photon flux density in the wavelength range of 520-570 nm to (ii) photosynthetic photon flux density, that is 65% or more.

Item 4:
The method according to any one of items 1-3, wherein the ratio is 75% or more.

Item 5:
The method according to item 4, wherein the ratio is 90% or more.

Item 6:
The method according to any one of items 1-5, wherein the artificial light has the maximum peak wavelength in the wavelength range of 520-570 nm.

Item 7:
The method according to any one of items 1-6, wherein the algal cells are irradiated with light in the wavelength range of 520-630 nm at a photon flux density of 50-3000 $\mu mol/m^2/s$.

Item 8:
The method according to any one of items 1-7, wherein the algal cells are irradiated with light in the wavelength range of 520-630 nm for a time period of 6-100 hours.

Item 9:
The method according to any one of items 1-8, wherein the artificial light comprises light having a wavelength spectrum with a peak wavelength at 545±25 nm and a half-width of 0.1-50 nm.

Item 10:
The method according to any one of items 1-9, wherein the light in the wavelength range of 520-630 nm comprises light emitted by a light-emitting diode or a laser diode.

Item 11:
The method according to any one of items 1-10, wherein the algal cells are irradiated with the light in the wavelength range of 520-630 nm at a first photon flux density value of 50-500 $\mu mol/m^2/s$ when the algal cells are present at a cell density of a predetermined value or less, and at a second photon flux density value of 300-3000 $\mu mol/m^2/s$, which is larger than the first photon flux density value, when the algal cells are present at a cell density of the predetermined value or more.

Item 12:
The method according to any one of items 1-11, wherein the algal cells are cultivated in a photobioreactor.

Item 13:
A method of cultivating algal cells, comprising further cultivating, in an open pond tank or a pond, the algal cells that have previously cultivated by the method according to item 12.

Item 14:
A method of providing an algal cell culture, comprising cultivating algal cells of an algae belonging to a class selected from Chlorophyceae, Euglenophyceae, Bacillariophyceae and Haptophyceae, by the method according to any one of items 1-13.

Item 15:
A photobioreactor for cultivating algal cells, comprising:
a reactor vessel configured to contain cells of an algae belonging to a class selected from Chlorophyceae, Euglenophyceae, Bacillariophyceae and Haptophyceae, and a culture medium for the algal cells; and
a lighting device configured to irradiate the reactor vessel with light and emit light having a ratio of (i) photon flux density in the wavelength range of 520-630 nm to (ii) photosynthetic photon flux density, that is 65% or more.

Item 16:
The photobioreactor according to item 15, wherein the lighting device is configured to emit light having a ratio of (i) photon flux density in the wavelength range of 520-570 nm to (ii) photosynthetic photon flux density, that is 65% or more.

Item 17:
The photobioreactor according to item 15 or 16, wherein the ratio is 75% or more.

Item 18:
The photobioreactor according to claim 17, wherein the ratio is 90% or more.

Item 19:
The photobioreactor according to any one of items 15-18, wherein the lighting device is configured to emit light having the maximum peak wavelength in the wavelength range of 520-570 nm.

Item 20:
The photobioreactor according to any one of items 15-19, wherein the lighting device comprises: a light source capable of emitting light with a peak wavelength in the wavelength range of 520-570 nm; and a control unit to control the light source to provide a photon flux density of 50-3000 µmol/m²/s in the wavelength range of 520-630 nm.

Item 21:

The photobioreactor according to item 20, further comprising a photosensor configured to detect light from the inside of the reactor vessel, wherein the control unit controls the light source according to the output of the photosensor.

Item 22:

The photobioreactor according to item 20 or 21, wherein the control unit controls the light source to emit the light in the wavelength range of 520-630 nm for a time period of 6-100 hours.

Item 23:

The photobioreactor according to any one of items 15-22, wherein the lighting device comprises a light source capable of emitting light having a wavelength spectrum with a peak wavelength at 545±25 nm and a half-width of 0.1-50 nm.

Item 24:

The photobioreactor according to item 23, wherein the light source is a light-emitting diode or a laser diode.

Item 25:

The photobioreactor according to any one of items 15-24, for use in the method according to claim 1.

Item 26:

A method of cultivating algal cells of an algae belonging to a class selected from Chlorophyceae, Euglenophyceae, Bacillariophyceae and Haptophyceae, according to any one of items 1-14, the method comprising:

irradiating the algal cells with an artificial light having a ratio of (i) photon flux density in the wavelength range of 520-630 nm to (ii) photosynthetic photon flux density, that is 65% or more; and measuring a condition of the algal cells and/or the condition of the algal cell culture, wherein the irradiation and non-irradiation of the algal cells with the artificial light are switched, or the photon flux density in the wavelength range of 520-630 nm is changed, according to the measured condition of the algal cells and/or the measured condition of the algal cell culture.

Item 27:

The method according to item 26, wherein the condition is at least one selected from the group consisting of cell density of the algal cell culture, singlet oxygen level of the algal cell culture, cell size of the algal cells and cell-cycle phase of the algal cells.

Item 28:

The method according to item 26 or 27, wherein the condition is the cell density of the algal cell culture, and wherein the photon flux density in the wavelength range of 520-630 nm of the light irradiated to the algal cells is a first photon flux density value when the cell density is a predetermined value or less and a second photon flux density value, which is larger than the first photon flux density value, when the cell density is the predetermined value or more.

Item 29:

The method according to item 28, further comprising measuring the singlet oxygen level of the algal cell culture, wherein a singlet oxygen eliminator is fed to the algal cell culture when the measured singlet oxygen level is a predetermined value or more.

Item 30:

The method according to item 28 or 29, wherein the first photon flux density value is 50-300 µmol/m²/s and the second photon flux density value is 300-900 µmol/m²/s.

Item 31:

The method according to item 26 or 27, wherein the condition is the singlet oxygen level of the algal cell culture, and wherein the photon flux density in the wavelength range of 520-630 nm of the light irradiated to the algal cells is decreased or the irradiation of the algal cells with the artificial light is stopped when the singlet oxygen level is above a first predetermined value, and the photon flux density in the wavelength range of 520-630 nm is increased or the algal cells are irradiated with the artificial light when the cell density is below a second predetermined value, which is smaller than the first predetermined value, or when a predetermined time period elapses.

Item 32:

The method according to item 26 or 27, wherein the condition is the cell size of the algal cells, and the method comprises size-classifying the algal cells between relatively small-sized algal cells and relatively large-sized algal cells and subjecting the relatively small-sized algal cells to a step $a_2$) and the relatively large-sized algal cells to a step $b_2$), and wherein the irradiation with the artificial light comprises:

the step $a_2$) of irradiating the relatively small-sized algal cells with the light in the wavelength range of 520-630 nm at a first photon flux density value; and the step $b_2$) of irradiating the relatively large-sized algal cells with the light in the wavelength range of 520-630 nm at a second photon flux density value, which is smaller than the first photon flux density value.

Item 33:

The method according to item 26 or 27, wherein the condition is the cell size of the algal cells and the method comprises size-classifying the algal cells between relatively small-sized algal cells and relatively large-sized algal cells, and wherein the relatively small-sized algal cells are subjected to a step $a_2$) of irradiation with the artificial light and the relatively large-sized algal cells are subjected to a step $b_2$) of placement in dim light or darkness.

Item 34:

The method according to item 32 or 33, wherein the algal cells previously subjected to the step $a_2$) are size-classified.

Item 35:

The method according to any one of items 32-34, wherein the algal cells previously subjected to the step $b_2$) are subjected to the step $a_2$) without size-classification.

Item 36:

The method according to item 26 or 27, wherein the condition is the cell-cycle phase of the algal cells and the method comprises synchronizing the cell-cycle phase of the algal cells, and wherein the irradiation with the artificial light comprises:

a step $a_3$) of irradiation with the light in the wavelength range of 520-630 nm at a first photon flux density value; and a step $b_3$) of irradiation with the light in the wavelength range of 520-630 nm at a second photon flux density value, which is smaller than the first photon flux density value, and wherein the synchronized algal cells are subjected to the step $a_3$) for a first predetermined time period and then to the step $b_3$) for a second predetermined time period, or subjected to the step $b_3$) for the second predetermined time period and then to the step $a_3$) for the first predetermined time period.

Item 37:

The method according to item 26 or 27, wherein the condition is the cell-cycle phase of the algal cells and the method comprises synchronizing the cell-cycle phase of the algal cells, and wherein the synchronized algal cells are subjected to a step $a_3$) of irradiation with the artificial light for a first predetermined time period and then to a step $b_3$)

of placement in dim light or darkness for a second predetermined time period, or subjected to the step $b_3$) for the second predetermined time period and then to the step $a_3$) for the first predetermined time period.

Item 38:

The method according to item 36 or 37, further comprising synchronizing the cell-cycle phase of the algal cells prior to the irradiation with the artificial light.

Item 39:

The method according to item 38, wherein the synchronization of the cell-cycle phase is carried out by pre-cultivating the algal cells in a predetermined light/dark cycle or treating the algal cells with a cell-cycle synchronizing agent.

Item 40:

The method according to any one of items 31-39, wherein the first photon flux density value is 300-900 μmol/m$^2$/s and the second photon flux density value is 50-300 μmol/m$^2$/s.

Item 41:

The method according to any one of items 31-40, wherein the algal cells are placed in dim light or darkness during the irradiation with the artificial light is stopped.

Item 42:

The method of cultivating algal cells of an algae belonging to a class selected from Chlorophyceae, Euglenophyceae, Bacillariophyceae and Haptophyceae, according to any one of items 1-14, the method comprising:

irradiating the algal cells with an artificial light having a ratio of (i) photon flux density in the wavelength range of 520-630 nm to (ii) photosynthetic photon flux density, that is 65% or more; and measuring a singlet oxygen level of the algal cell culture, wherein a singlet oxygen eliminator is fed to the algal cell culture when the measured singlet oxygen level is a predetermined value or more.

Item 43:

A method of cultivating algal cells, comprising further cultivating, in an open pond tank or a pond, the algal cells that have previously cultivated in a photobioreactor by the method according to any one of items 26-42.

Item 44:

A method of providing an algal cell culture, comprising cultivating algal cells of an algae belonging to a class selected from Chlorophyceae, Euglenophyceae, Bacillariophyceae and Haptophyceae, by the method according to any one of items 26-43.

Item 45:

A photobioreactor for cultivating algal cells, comprising:

a reactor vessel configured to contain cells of an algae belonging to a class selected from Chlorophyceae, Euglenophyceae, Bacillariophyceae and Haptophyceae, and a culture medium for the algal cells;

a lighting device configured to irradiate the reactor vessel with light having a ratio of (i) photon flux density in the wavelength range of 520-630 nm to (ii) photosynthetic photon flux density, that is 65% or more, which lighting device comprises a light source capable of emitting light with a peak wavelength in the wavelength range of 520-630 nm and a control unit to control the light source; and a sensor configured to measure a condition of the algal cells and/or a condition of the algal cell culture in the reactor vessel, wherein the control unit controls the light source according to the output of the sensor.

Item 46:

The photobioreactor according to item 45, wherein the control unit controls the light source to change the photon flux density in the wavelength range of 520-630 nm according to the output of the sensor.

Item 47:

The photobioreactor according to item 45 or 46, wherein the sensor is a photosensor.

Item 48:

The photobioreactor according to any one of items 45-47, wherein the condition is at least one selected from the group consisting of cell density of the algal cell culture, singlet oxygen level of the algal cell culture, cell size of the algal cells and cell-cycle phase of the algal cells.

Item 49:

A photobioreactor for cultivating algal cells, comprising:

a reactor vessel configured to contain cells of an algae belonging to a class selected from Chlorophyceae, Euglenophyceae, Bacillariophyceae and Haptophyceae, and a culture medium for the algal cells;

a lighting device configured to irradiate the reactor vessel with light having a ratio of (i) photon flux density in the wavelength range of 520-630 nm to (ii) photosynthetic photon flux density, that is 65% or more; and a size classifier configured to classify the algal cells by size, wherein the size classifier is interconnected to the reactor vessel and the relatively small-sized algal cells classified by the size classifier are fed to the reactor vessel.

Item 50:

The photobioreactor according to item 49, wherein the lighting device (first lighting device) is configured to irradiate light in the wavelength range of 520-630 nm at a first photon flux density value, and the photobioreactor further comprises:

a second reactor vessel configured to contain the algal cells and a culture medium for the algal cells; and a lighting device (second lighting device) configured to irradiate the second reactor vessel with light in the wavelength range of 520-630 nm at a second photon flux density value, which is smaller than the first photon flux density value;

wherein the first reactor vessel is connected to the second reactor vessel via the size classifier and wherein the relatively small-sized algal cells classified by the size classifier are fed to the first reactor vessel and the relatively large-sized algal cells classified by the size classifier are fed to the second reactor vessel.

Item 51:

The photobioreactor according to item 49, further comprising:

a second reactor vessel configured to contain the algal cells and a culture medium for the algal cells, wherein the second reactor vessel is formed of, or covered or surrounded with, a material having a low visible light transmittance to make the inside of the second reactor vessel dim or dark, wherein the reactor vessel defined in item 49 (first reactor vessel) is connected the second reactor vessel via the size classifier to and wherein the relatively small-sized algal cells classified by the size classifier are fed to the first reactor vessel and the relatively large-sized algal cells classified by the size classifier are fed to the second reactor vessel.

Item 52:

The photobioreactor according to claim 50 or 51, wherein the first reactor vessel is interconnected to the second reactor vessel via the size classifier.

Item 53:

A photobioreactor for cultivating algal cells, comprising:

a reactor vessel configured to contain cells of an algae belonging to a class selected from Chlorophyceae, Euglenophyceae, Bacillariophyceae and Haptophyceae, and a culture medium for the algal cells;

a lighting device configured to irradiate the reactor vessel with light having a ratio of (i) photon flux density in the wavelength range of 520-630 nm to (ii) photosynthetic photon flux density, that is 65% or more;

a sensor configured to measure a singlet oxygen level in the reactor vessel; and a singlet oxygen eliminator-feeder configured to feed a singlet oxygen eliminator to the reactor vessel, wherein the feeding of the singlet oxygen eliminator from the singlet oxygen eliminator-feeder to the reactor vessel is controlled according to the output of the sensor.

Item 54:

The photobioreactor according to any one of items 45-53, for use in the method according to any one of items 26-44.

EXAMPLES

Experiment 1: Measurement of Absorption Spectrum of *Chlamydomonas* Cells

Methods

*Chlamydomonas* cells (*Chlamydomonas reinhardtii* CC-125) were precultivated in a bottle photobioreactor for 3 days under the following conditions:

Precultivation Conditions:

Light: White fluorescent light (photon flux density: 200 μmol/m$^2$/s)

Cultivation medium: 500 mL of a modified HSM medium which is 5-fold increased nitrogen source obtained by adding up to 2.5 g/L of NH4Cl $CO_2$ concentration: 2% (v/v) $CO_2$ fed to the medium at a rate of 0.1 mL/mL medium/min Temperature: 30° C.

Stirring: 500 rpm

After the precultivation, the liquid culture was diluted to give an optical density at 750 nm ($OD_{750}$) of 0.4, corresponding to 0.15 g/L expressed in terms of dry weight, and then subjected to main cultivation.

The main cultivation was carried out for 2 days under the following conditions.

Main cultivation conditions ($OD_{750}$=0.4 at the start):

Light: White fluorescent light (photon flux density: 200 μmol/m$^2$/s)

Cultivation medium: 500 mL of a modified HSM medium which is 5-fold increased nitrogen source obtained by adding up to 2.5 g/L of NH4Cl $CO_2$ concentration: 2% (v/v) $CO_2$ fed to the medium at a rate of 0.1 mL/mL medium/min Temperature: 30° C.

Stirring: 500 rpm

Figure 2:
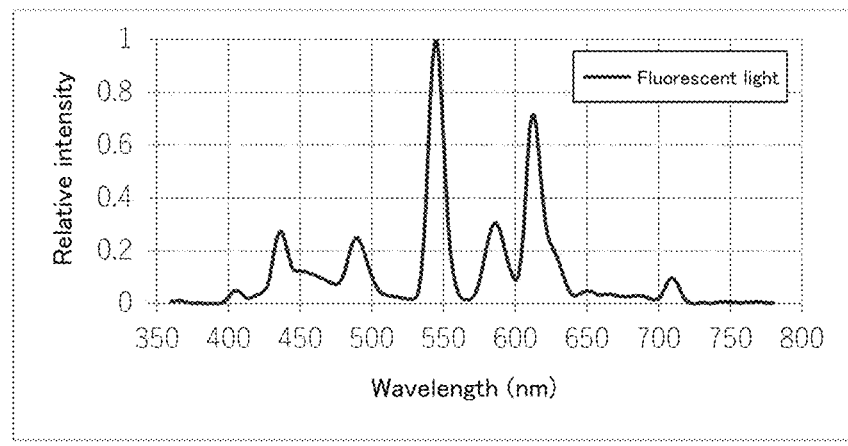
FIG. 2 illustrates the emission spectrum of the white fluorescent lamp used in Experiment 1.

FIG. 2 shows the emission spectrum of the white fluorescent lamp (model: FL20SSEX-N/18-X, NEC Lighting Ltd.) used for the precultivation and the main cultivation.

After 2 days of main cultivation, 100 μL of the liquid culture was taken in a 96-well microplate and the absorption spectrum was measured on an absorbance microplate reader.

Results

Figure 3:
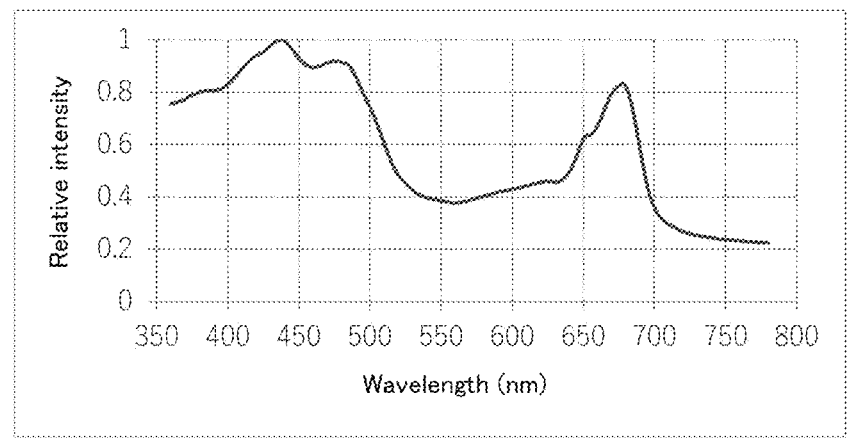
FIG. 3 illustrates the absorption spectrum of *Chlamydomonas* algae.

The resulting absorption spectrum of the cultivated *Chlamydomonas* cells is shown in FIG. 3.

The absorption spectrum confirms that *Chlamydomonas* cells exhibit strong absorption due to chlorophylls and carotenoids, while having weak absorption in the range of about 520 to about 630 nm (including green light).

Experiment 2: Effects of Green Light and Red Light on the Cultivation of Chlorophyceae Cells Methods

*Chlamydomonas* cells (*Chlamydomonas reinhardtii* CC-125) were precultivated for 3 days in the same manner as in Experiment 1.

Main cultivation was carried out for 5 to 12 days under the same cultivation conditions as in Experiment 1, except that the following LED lights were used:

LED light 1 having a peak wavelength of 530 nm at a photon flux density of 100, 200 or 600 μmol/m$^2$/s; and LED light 2 having a peak wavelength of 660 nm at a photon flux density of 100, 200 or 600 μmol/m$^2$/s.

Figure 4:
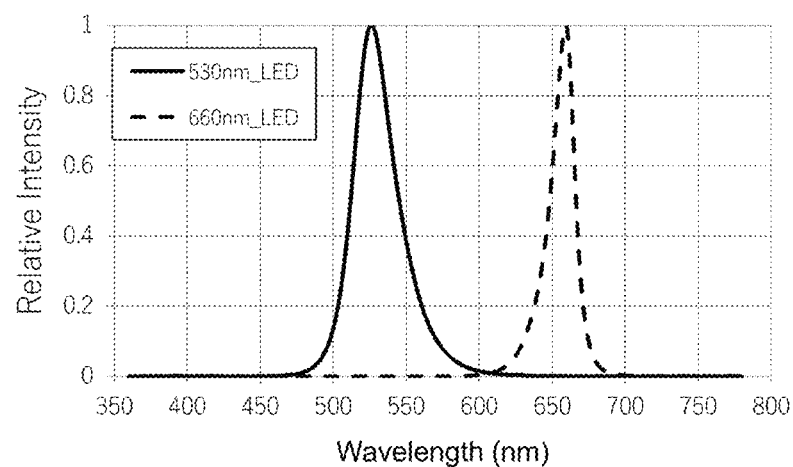
FIG. 4 illustrates the emission spectra of the two LEDs used in Experiment 2.

For irradiating LED light 1 and LED light 2, an LED (model: NCSG119B-V1, Nichia Corporation) and a commercially available LED (model: LXM3-PD01, Lumileds) were used, respectively, the emission spectra of which are given in FIG. 4.

Every 24 hours after starting the main cultivation, a sample (approximately 10 mL) of each of the liquid cultures was taken from the reactor vessel and centrifuged (at 5,000×g for 1 min) to collect *Chlamydomonas* cells. The collected cells were washed once with distilled water and then freeze-dried. The dry weight was measured to calculate biomass (g/L).

Results

Figure 5A:
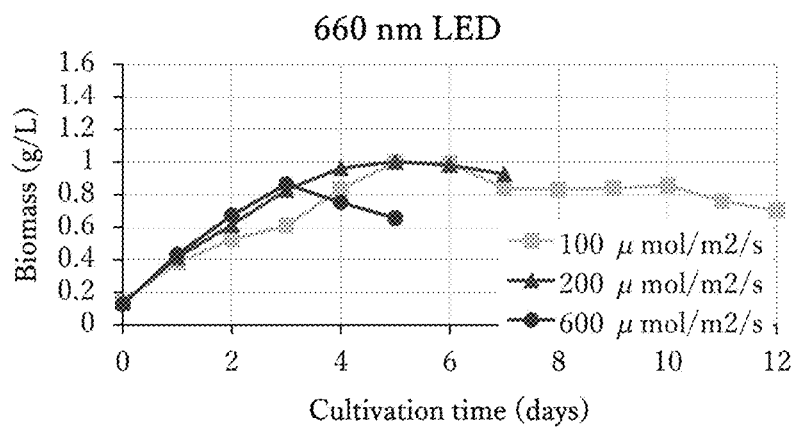
FIG. 5A shows the time course of cell mass (biomass) in *Chlamydomonas* cells cultivated under irradiation with LED light having a center wavelength of 660 nm (660 nm LED).
Figure 5B:
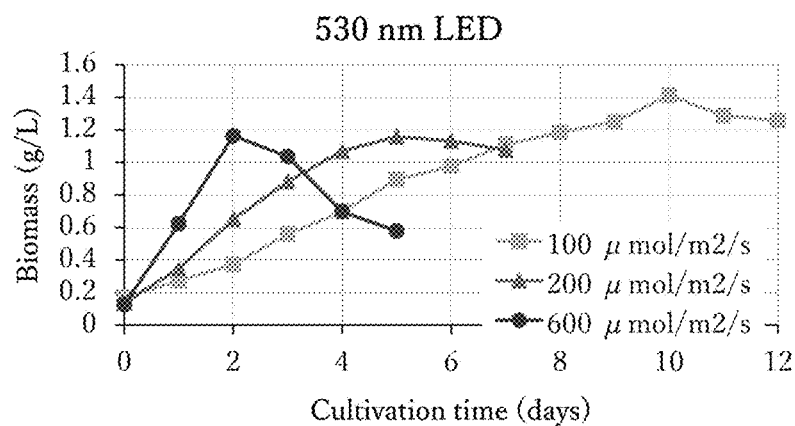
FIG. 5B shows the time course of cell mass (biomass) in *Chlamydomonas* cells cultivated under irradiation with LED light having a center wavelength of 530 nm (530 nm LED).

FIGS. 5A and 5B show the time courses of biomass in *Chlamydomonas* cultures, cultivated under the irradiation with LED light having a center wavelength of 660 nm or 530 nm, respectively.

Under the irradiation with light having a center wavelength of 660 nm, increasing photon flux density had little effect on the rate of biomass growth of *Chlamydomonas* culture and the biomass did not increase above 1.0 g/L (FIG. 5A).

Under the irradiation with light having a center wavelength of 530 nm, increasing photon flux density led to a higher rate of biomass growth (FIG. 5B). After 2 days of cultivation with light at a photon flux density of 600 μmol/m$^2$/s, the biomass of *Chlamydomonas* culture was 1.2 g/L. In addition, the biomass increased above 1.0 g/L at any of the photon flux density values, and up to 1.4 g/L at 100 μmol/m$^2$/s.

As can be seen from the results, cultivation of cells of an algae belonging to a class selected from Chlorophyceae, Euglenophyceae, Bacillariophyceae and Haptophyceae with light in the wavelength range of 520 to 630 nm (and more particularly 520 to 600 nm) results in increasing the growth rate and/or the maximum of biomass of the algal cell culture. It is found that the algae that have chlorophyll, but not phycobilin, as a photosynthetic pigment can be cultivated efficiently by irradiation with light in the wavelength range of 520 to 630 nm (and more particularly 520 to 600 nm).

Light in the wavelength range of 520 to 630 nm can reach deeper into liquid algal culture because the light in this wavelength range is less likely to be absorbed by algal cells (FIG. 3) and therefore the light transmittance is not significantly reduced in the culture even when the cells are grown and the cell density is high. Without wishing to be bound by any particular theory, the present inventors believe that light in said wavelength range is used for the photosynthesis in the algal cells, thereby they can grow to a higher cell density than when cultivated with red light irradiation.

It is known that red light at a high photon flux density generates active oxygen species in cells and therefore the cells are damaged. Without wishing to be bound by any particular theory, the present inventors believe that light in the wavelength range of 520 to 630 nm generates only a small amount of active oxygen species in cells and therefore the cells are less likely to be damaged, resulting in less inhibition of cell growth. This indicates that increasing the photon flux density of light in the wavelength range of 520 to 630 nm irradiated to algal cells can facilitate the cell growth.

Experiment 3: Effects of Green Light Plus White Light on the Cultivation of Chlorophyceae Cells Methods Chlamydomonas cells (Chlamydomonas reinhardtii CC-125) were precultivated for 3 days in the same manner as in Experiment 1.

Main cultivation was carried out for 6 days under the same conditions as in Experiment 1, except that the following LED lights were used:

LED light 3: white LED light at a photon flux density of 200 $\mu mol/m^2/s$; and LED light 4: while LED light at a photon flux density of 150 $\mu mol/m^2/s$+LED light with a peak wavelength of 530 nm at a photon flux density of 50 $\mu mol/m^2/s$ (simultaneous irradiation)

For irradiating white LED light, an LED (model: NF2W757G-F1, Nichia Corporation) was used. For irradiating LED light with a peak wavelength of 530 nm, an LED (model: NCSG119B-V1, Nichia Corporation) was used.

Figure 6:
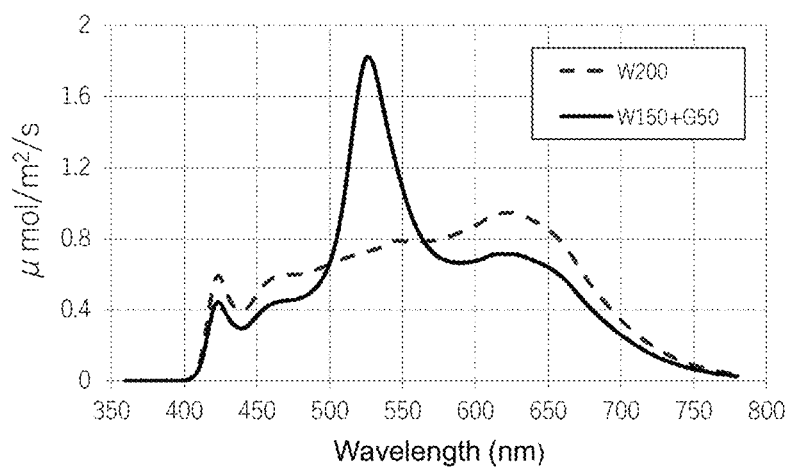
FIG. 6 illustrates the emission spectra of the LEDs used in Experiment 3.

FIG. 6 shows the emission spectra of the LEDs used.

Every 24 hours after starting the main cultivation, a sample (approximately 10 mL) of each of the liquid cultures was taken from the reactor vessel and centrifuged (at 5,000×g for 1 min) to collect Chlamydomonas cells. The collected Chlamydomonas cells were washed once with distilled water and then freeze-dried. The dry weight was measured to calculate biomass (g/L).

Results

Figure 7:
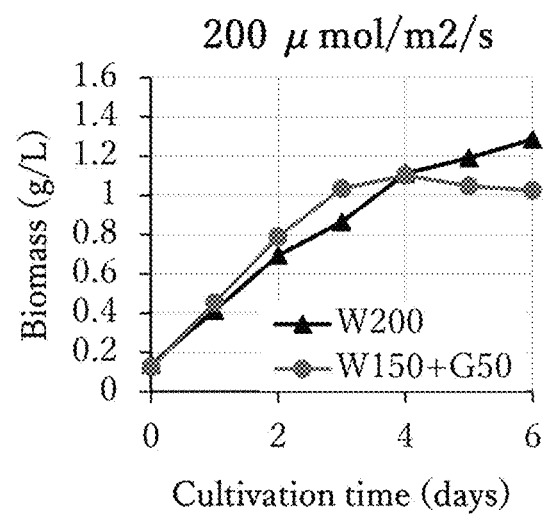
FIG. 7 illustrates the time course of cell mass (biomass) in *Chlamydomonas* cells cultivated under two different irradiations.

FIG. 7 shows the time course of cell mass (biomass) in Chlamydomonas cultures cultivated under the irradiation with the two kinds of light.

The results confirm that irradiation of Chlamydomonas cells in culture with light having a peak wavelength at 530 nm plus white light increases the initial growth rate of biomass in the cells. This indicates that irradiation with light with a higher percentage of wavelengths from 520 to 630 nm (more particularly from 520 to 600 nm) can cause a faster growth of cells of an algae belonging to a class selected from Chlorophyceae, Euglenophyceae, Bacillariophyceae and Haptophyceae.

Experiment 4: Generation of Singlet Oxygen in Chlorophyceae Cells by Irradiation with Red Light and Green Light Methods Chlamydomonas cells (Chlamydomonas reinhardtii CC-125) were subjected to the precultivation and the main cultivation for a total of 5 days as in Experiment 1, except that 450 mL of the HSM medium was used.

After the main cultivation, the liquid cultures were diluted to give an optical density at 750 nm ($OD_{750}$) of 1.0 and left to stand in dark for 1 hour. After the addition of Singlet Oxygen Sensor Green (SOSG; Singlet Oxygen Sensor Green-Special Packaging, Invitrogen™) at a final concentration of 50 $\mu$M, the diluted cultures were subjected to further cultivation in a 12-well plate for 12 hours under the following conditions.

Light: Green LED light with a peak wavelength of 530 nm at a photon flux density of 600 $\mu mol/m^2/s$ Red LED light with a peak wavelength of 660 nm at a photon flux density of 600 $\mu mol/m^2/s$ (The LEDs used in Experiment 4 are the same types of the LEDs used in the Experiment 2.)

Non-irradiation

Cultivation medium: 1 mL of the modified HSM medium which is 5-fold increased nitrogen source obtained by adding up to 2.5 g/L of NH4Cl $CO_2$ concentration: Not fed Temperature: 30° C.

Stirring: 100 rpm

After the further cultivation, SOSG fluorescence (excitation wavelength: 488 nm; detection wavelength: 525/50 nm) was analyzed on a Cell Sorter SH800 (SONY).

Figure 8:
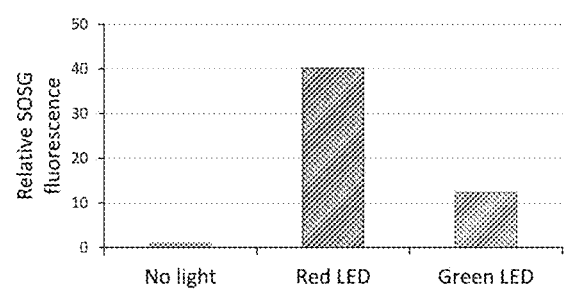
FIG. 8 illustrates the relative SOSG fluorescence from *Chlamydomonas* cells irradiated with red LED light or green LED light or un-irradiated.

Results:

FIG. 8 shows the SOSG fluorescence from the algal cells irradiated with red LED light or green LED light, relative to that from the un-irradiated algal cells (defined as 1).

The relative SOSG fluorescence is 40.1 for the algal cells irradiated with red LED light and 12.4 for the algal cells irradiated with green LED light.

The data suggest that the amount of singlet oxygen generated in the algal cells by green light irradiation is less than that by red light irradiation. The data also suggest that regardless of whether green or red light, too high energy irradiation causes a high level of singlet oxygen generation in the algal cells, resulting in an adverse effect on the growth rate (and, therefore, on the rate of biomass increase). Controlling the singlet oxygen level and the irradiance can enable an efficient cultivation of algal cells.

Experiment 5: Correlation Between the Level of Singlet Oxygen Generation and the Cell Cycle Phases Methods Chlamydomonas cells (Chlamydomonas reinhardtii CC-125) were cultivated as in Experiment 4, except that red LED light was not used in the further cultivation.

After the further cultivation, DNA in the cells was fluorescently stained with 4',6-diamidino-2-phenylindole (DAPI).

The SOSG fluorescence (excitation wavelength: 488 nm; detection wavelength: 525/50 nm), DAPI fluorescence (excitation wavelength: 405 nm; detection wavelength: 450/50 nm) and chlorophyll fluorescence (excitation wavelength: 488 nm; detection wavelength: 720/60 nm) were analyzed on a Cell Sorter SH800 (SONY).

Figure 9A:
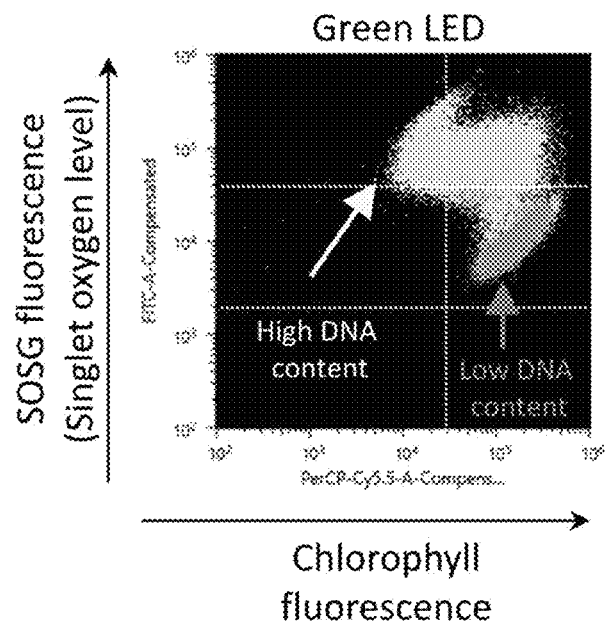
FIG. 9A illustrates flow cytometric cytogram of SOSG fluorescence versus chlorophyll fluorescence from *Chlamydomonas* cells irradiated with green LED light.
Figure 9B:
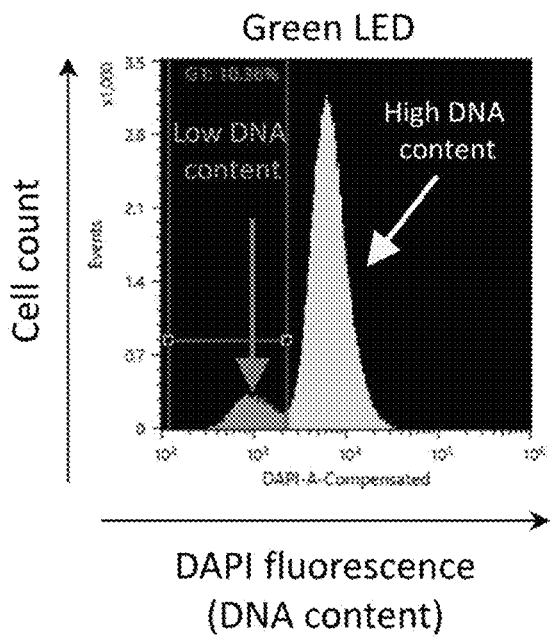
FIG. 9B illustrates flow cytometric histogram of DAPI fluorescence from *Chlamydomonas* cells irradiated with green LED light.
Figure 9C:
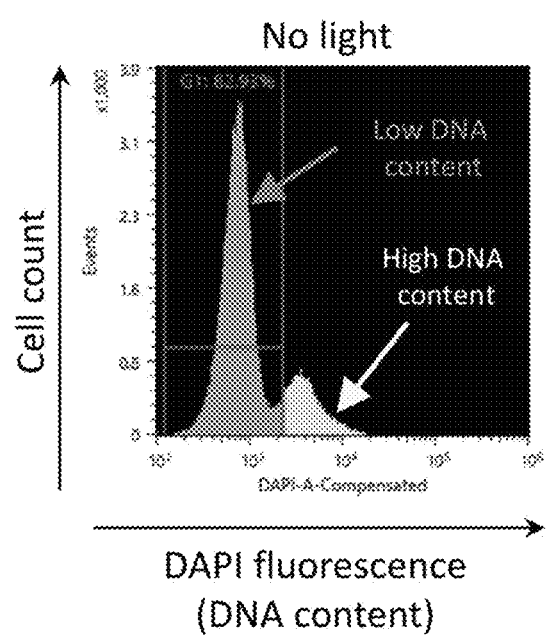
FIG. 9C illustrates flow cytometric histogram of DAPI fluorescence from *Chlamydomonas* cells un-irradiated (No light).

Results:

The results are shown in FIGS. 9A to 9C. FIG. 9A illustrates flow cytometric cytogram of SOSG fluorescence versus chlorophyll fluorescence from Chlamydomonas cells irradiated with green LED light. FIGS. 9B and 9C illustrates flow cytometric histograms of DAPI fluorescence from Chlamydomonas cells irradiated with green LED light or un-irradiated (No light).

The cells with a strong SOSG fluorescence (that is, the cells with a high level of singlet oxygen generation) tend to exhibit a strong DAPI fluorescence (i.e., to have a high DNA content) and a weak chlorophyll fluorescence (i.e., to have a low chlorophyll content) (FIG. 9A).

The irradiation with green LED light (at a photon flux density of 600 μmol/m²/s) for 12 hours increased the percentage of the cells with a strong SOSG fluorescence (that is, the cells with a high level of singlet oxygen generation) (FIGS. 8 and 9A) as well as the percentage of the cells with a strong DAPI fluorescence (that is, the cells having a high DNA content) (FIG. 9B vs. FIG. 9C).

Without wishing to be bound by any particular theory, the present inventors believe from the results that an increased level of singlet oxygen causes oxidative damage to the algal cells, resulting in cell cycle arrest at the phases when the DNA content is high (the S, G2 and/or M phases) and (simultaneously or subsequently) the decrease of chlorophyll content. Controlling irradiance according to the cell-cycle phases can enable an efficient cultivation of algal cells.

Experiment 6: Analysis of Pigments Contained in *Chlamydomonas* Cells Cultivated Under the Irradiation with Red LED Light or Green LED Light Methods

*Chlamydomonas* cells (*Chlamydomonas reinhardtii* CC-125) were cultivated as in Experiment 2, except that 450 mL of the HSM medium was used, the only photon flux density of LED light was 600 μmol/m²/s and the time period of the main cultivation was 2 days.

*Chlamydomonas* cells were collected by centrifugation (at 50,000×g for 1 minute) from each of the cultures after the preliminary cultivation and on day 1 of the main cultivation. The collected cells were washed once with distilled water and then freeze-dried.

About 5 g of freeze-dried algal cells were placed into a lysis microtube, to which then added were a 300 μL volume of glass beads and 500 μL of a 1:1 mixture of acetone and methanol. The cells were homogenized using a multibeads shocker under the following conditions: 30 cycles of 60 sec ON (2,700 rpm)+60 sec OFF (0 rpm) at 4° C.

After the homogenates were centrifuged (10,000×g, 5 min., 4° C.), the supernatants were collected.

One hundred fifty microliters of the supernatants were evaporated to dryness in a centrifugal evaporator, followed by re-dissolution in 50 μL of chloroform. To each of the thus-obtained solutions, 425 μL of a 2:8 mixture of chloroform and acetonitrile and 25 μL of 20 M trans-β-apo-8'-carotenal (as internal standard) were added. The pigments in the solutions were analyzed by UPLC (ACQUITY UPLC system: Waters) under the following conditions. UPLC/PDA analytic conditions Mobile phase: Eluent A: MeOH:H₂O=1:1 (v/v)

Eluent B: AcCN

| Gradient: | Time (min.) | 0 | 9 |
|---|---|---|---|
| | Eluent A (%) | 50 | 0 |
| | Eluent B (%) | 50 | 100 |

Column: BEH shield RP18 (1.7 μm, 2.1 mm×100 mm)

Flow rate: 0.6 mL/min.

Injection: 5 μL

Column temperature: 30° C.

Detector: photodiode array (PDA; Waters): 445 nm

Figure 10A:
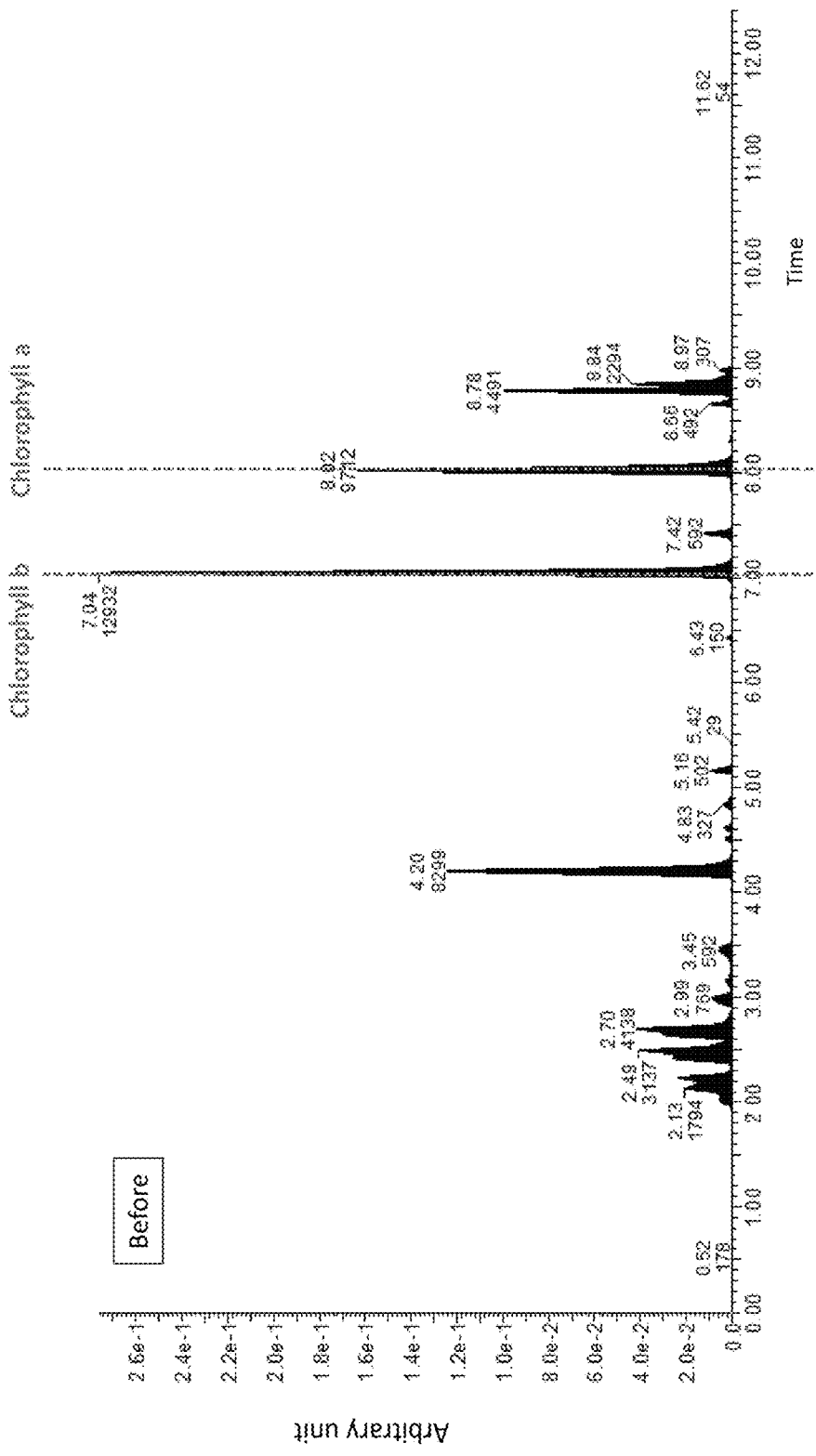
FIG. 10A illustrates the liquid chromatogram of the pigments obtained from *Chlamydomonas* cells before the main cultivation.
Figure 10B:
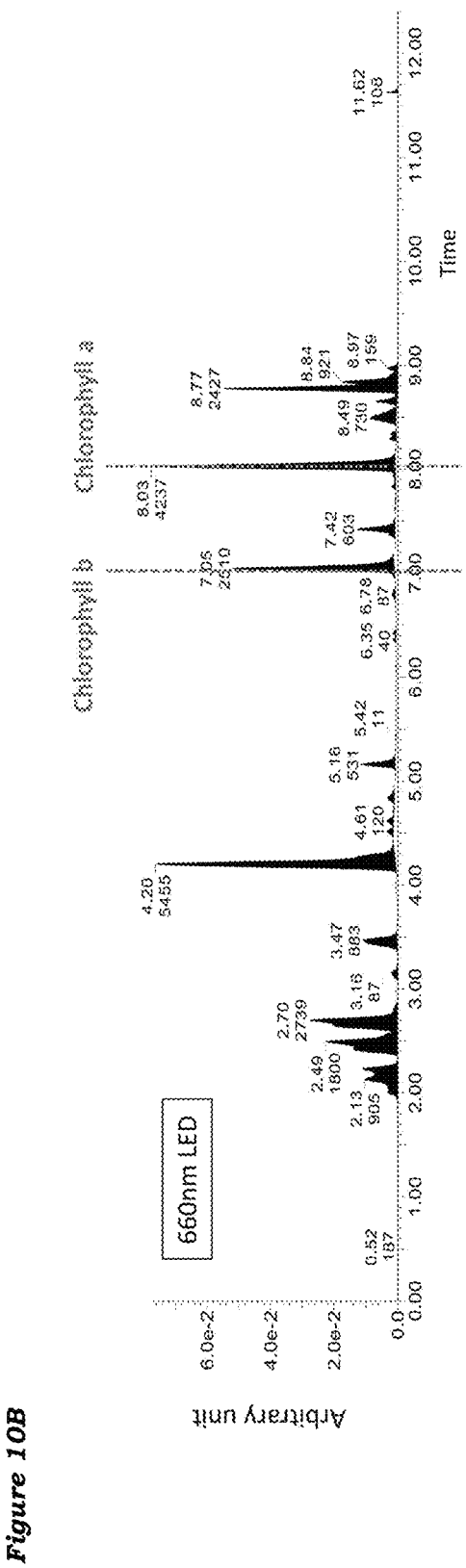
FIG. 10B illustrates the liquid chromatogram of the pigments obtained from *Chlamydomonas* cells after cultivation under irradiation with LED light having a center wavelength of 660 nm.
Figure 10C:
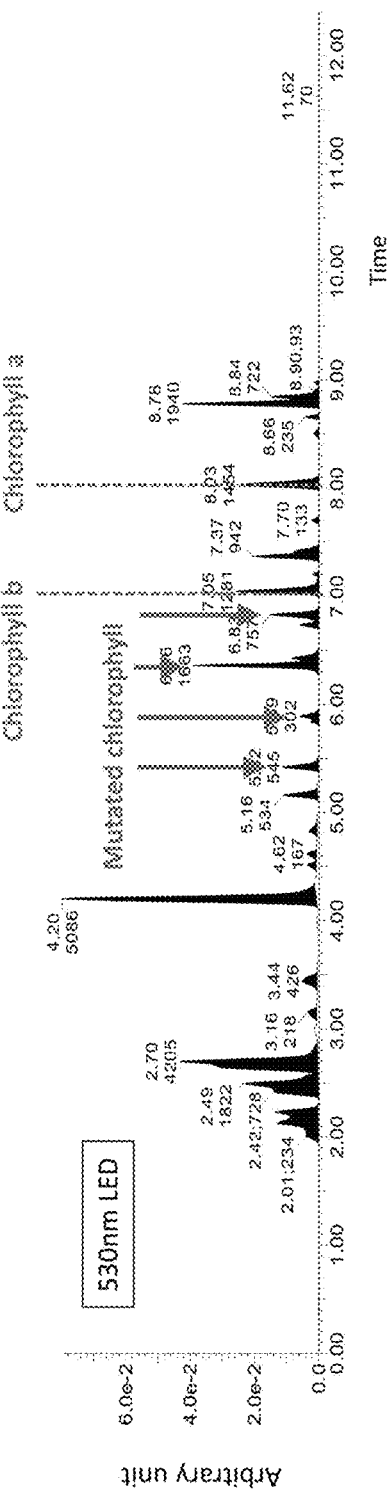
FIG. 10C illustrates the liquid chromatograms of the pigments obtained from *Chlamydomonas* cells after cultivation under irradiation with LED light having a center wavelength of 530 nm.

Results:

The resulting liquid chromatograms are given in FIGS. 10A to 10C.

In the algal cells cultivated under green light irradiation, the native chlorophylls were decreased while mutated chlorophylls appeared (FIG. 10C vs. FIGS. 10A and 10B).

The algal cells having decreased native chlorophylls might have improved in transmittance of red to blue light and therefore be efficiently cultivated, especially under the artificial irradiation.

Experiment 7: Algal Cell Cultivation with an Na Lamp

Methods

*Chlamydomonas* cells (*Chlamydomonas reinhardtii* CC-125) were cultivated as in Experiment 2, except that 450 mL of the HSM medium was used, the algal cells were irradiated with Na lamp light with a peak wavelength of 589 nm at a photon flux density of 600 μmol/m²/s and the time period of the main cultivation was 4 days.

Figure 11:
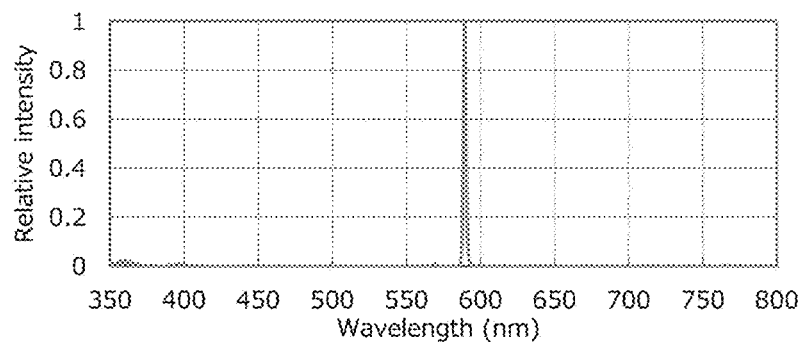
FIG. 11 illustrates the emission spectrum of Na light used in Experiment 7.

The Na lamp used was a low-pressure sodium lamp (NX35, Panasonic), the emission spectrum of which is given in FIG. 11.

A sample (about 8 mL) of the culture was taken from the culture vessel on each day during the main cultivation, and centrifuged (at 50,000×g for 1 minute) to collect *Chlamydomonas* cells. The collected cells were washed once with distilled water and freeze-dried, and then weighed to calculate biomass.

Figure 12A:
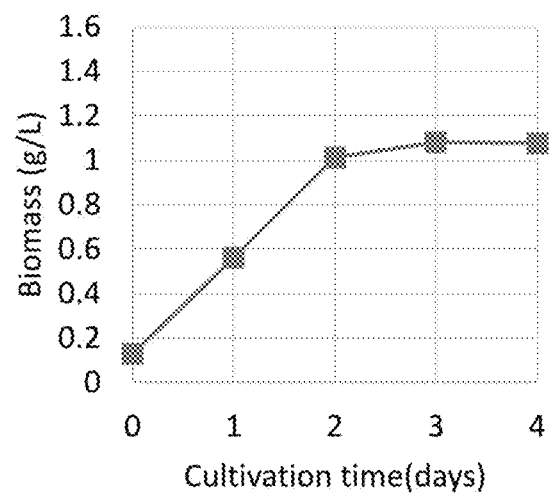
FIG. 12A illustrates the time course of cell mass (biomass) in the *Chlamydomonas* cells cultivated under irradiation with Na lamp light (peak wavelength: 589 nm).
Figure 12B:
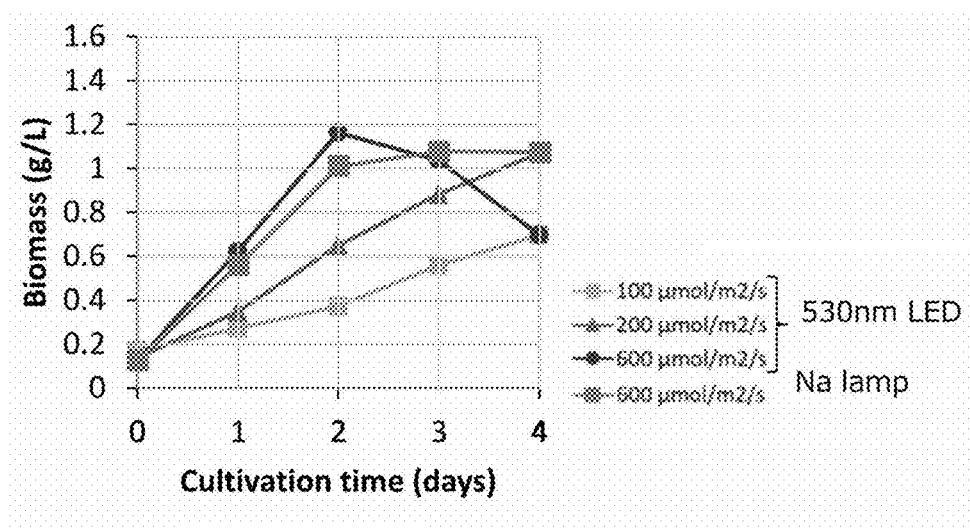
FIG. 12B illustrates the time courses as indicated in FIG. 5, overlaid on the time course as indicated in FIG. 12A.

Results:

FIG. 12A shows the time course of biomass in the *Chlamydomonas* cells cultivated for 4 days under irradiation with Na lamp light (peak wavelength: 589 nm; photon flux density: 600 μmol/m²/s). FIG. 12B collectively shows the results obtained with Na lamp light and with LED light (peak wavelength: 530 nm) in Experiment 2.

In the cells cultivated under irradiation with Na lamp light for 2 days, the biomass exceeded 1.0 g/L.

The time course of biomass in the Chlorophyceae cells cultivated under irradiation with Na lamp light is similar to that in the Chlorophyceae cells cultivated under irradiation with green LED light.

These results suggest that the irradiation with light in the wavelength range of 520 to 630 nm is effective for efficient cultivation of algal cells irrespective of the type of light source.

The contents of all patents, patent applications and references cited in the present specification are incorporated herein in its entirety by reference, as if fully and specifically set forth herein, to the fullest extent permitted by applicable law.

It is to be noted that the above embodiments and examples are given by way of illustration only for the purpose of better understanding of the invention. It is to be also understood that the present invention is not limited to the particular configurations, arrangements, process steps, materials, means and devices described in the specification and the appended drawings.

Various other changes, modifications and alterations can be made to the embodiments described above without departing from the spirit and scope of the present invention. It is to be further noted that aspects of the invention described with respect to one embodiment, may be incorporated in a different embodiment although not specifically described relative thereto. That is, all embodiments and/or features of any embodiment can be combined in any way and/or combination.

What is claimed is:

1. A method of cultivating algal cells of an algae belonging to a class selected from Chlorophyceae, Euglenophyceae, Bacillariophyceae and Haptophyceae, the method comprising:
   irradiating the algal cells with an artificial light having a ratio of (i) photon flux density in a wavelength range of 520-630 nm to (ii) photosynthetic photon flux density, that is 65% or more; and
   measuring a cell density of an algal cell culture provided by cultivating the algal cells,
   wherein the photon flux density in the wavelength range of 520-630 nm of the light irradiated to the algal cells is set to be a first photon flux density value when the cell density is a predetermined value or less, and is set to be a second photon flux density value, which is larger than the first photon flux density value, when the cell density is the predetermined value or more.

2. The method according to claim 1, further comprising:
   measuring singlet oxygen level of the algal cell culture,
   wherein a singlet oxygen eliminator is fed to the algal cell culture when the measured singlet oxygen level is a predetermined value or more.

3. The method according to claim 1, wherein the first photon flux density value is in a range of 50-300 $\mu mol/m^2/s$ and the second photon flux density value is in a range of 300-900 $\mu mol/m^2/s$.

4. The method according to claim 1, wherein the algae belong to a class selected from Chlorophyceae or Euglenophyceae.

5. The method according to claim 1, wherein the artificial light has a ratio of (i) photon flux density in a wavelength range of 520-570 nm to (ii) photosynthetic photon flux density, that is 65% or more.

6. The method according to claim 1, wherein the ratio is 75% or more.

7. The method according to claim 6, wherein the ratio is 90% or more.

8. The method according to claim 1, wherein the artificial light has a maximum peak wavelength in a wavelength range of 520-570 nm.

9. The method according to claim 1, wherein each of the first photon flux density and the second photon flux density is in a range of 50-3000 $\mu mol/m^2/s$.

10. The method according to claim 1, wherein the algal cells are irradiated with light in the wavelength range of 520-630 nm for a time period of 6-100 hours.

11. The method according to claim 1, wherein the artificial light comprises light having a wavelength spectrum with a peak wavelength in a wavelength range of 520-570 nm and a half-width of 0.1-50 nm.

12. The method according to claim 1, wherein the light in the wavelength range of 520-630 nm comprises light emitted by a light-emitting diode or a laser diode.

13. The method according to claim 1, wherein the first photon flux density value is in a range of 50-500 $\mu mol/m^2/s$ and the second photon flux density value is in a range of 300-3000 $\mu mol/m^2/s$.

14. The method according to claim 1, wherein the algal cells are cultivated in a photobioreactor.

15. A method of cultivating algal cells, comprising further cultivating, in an open pond tank or a pond, the algal cells that have been previously cultivated in a photobioreactor by the method according to claim 1.

* * * * *